US009410164B2

(12) United States Patent
Boisart, Sr. et al.

(10) Patent No.: US 9,410,164 B2
(45) Date of Patent: Aug. 9, 2016

(54) BIOSYNTHESIS PATHWAY FOR PRENOL IN A RECOMBINANT MICROORGANISM

(71) Applicant: METABOLIC EXPLORER, Saint Beauzire (FR)

(72) Inventors: Cedric Boisart, Sr., Gerzat (FR); Guillaume Letellier, Volvic (FR)

(73) Assignee: METABOLIC EXPLORER, Saint Beauzire (FR)

( * ) Notice: Subject to any disclaimer, the term of this patent is extended or adjusted under 35 U.S.C. 154(b) by 286 days.

(21) Appl. No.: 14/350,429

(22) PCT Filed: Oct. 11, 2012

(86) PCT No.: PCT/EP2012/070160
§ 371 (c)(1),
(2) Date: Apr. 8, 2014

(87) PCT Pub. No.: WO2013/053824
PCT Pub. Date: Apr. 18, 2013

(65) Prior Publication Data
US 2014/0256008 A1    Sep. 11, 2014

Related U.S. Application Data

(60) Provisional application No. 61/545,789, filed on Oct. 11, 2011.

(30) Foreign Application Priority Data

Oct. 11, 2011    (EP) .................................... 11306313

(51) Int. Cl.
*C12P 7/16*    (2006.01)
*C12P 7/04*    (2006.01)

(52) U.S. Cl.
CPC ... *C12P 7/04* (2013.01); *C12P 7/16* (2013.01); *Y02E 50/10* (2013.01)

(58) Field of Classification Search
CPC combination set(s) only.
See application file for complete search history.

(56) References Cited

U.S. PATENT DOCUMENTS

| 2008/0092829 A1† | 4/2008 | Renninger |
| 2010/0216958 A1 | 8/2010 | Peters et al. |
| 2010/0304450 A1 | 12/2010 | Eiteman et al. |

FOREIGN PATENT DOCUMENTS

| WO | 2004076659 A2 | 9/2004 |
| WO | 2005047498 A1 | 5/2005 |
| WO | 2005073364 A2 | 8/2005 |
| WO | 2005111202 A1 | 11/2005 |
| WO | 2006082252 A2 | 8/2006 |
| WO | 2006082254 A2 | 8/2006 |
| WO | 2007017710 A1 | 2/2007 |
| WO | 2007077041 A1 | 7/2007 |
| WO | 2007141316 A2 | 12/2007 |
| WO | 2007144346 A1 | 12/2007 |
| WO | 2008040387 A1 | 4/2008 |
| WO | 2008052595 A1 | 5/2008 |
| WO | 2008052973 A2 | 5/2008 |
| WO | 2009006429 A1 | 1/2009 |
| WO | 2009076676 A2 | 6/2009 |
| WO | 2010031076 A2 | 3/2010 |

OTHER PUBLICATIONS

Amann et al., (1983), Gene. 25:167-178.
Amann et al., (1988), Gene. 69:301-315.
Anderson EH et al., (1946), Proc Natl Acad Sci USA. 32:120-128.
Bode HB et al., (2009), Chembiochem. 10:128-140.
Däschner K. et al., (2001), Plant Physiol. 126:601-612.
Datsenko KA et al., (2000), Proc Natl Acad Sci USA. 97:6640-6645.
Dhar A. et al., (2002), J Ind Microbiol Biotechnol. 28:81-87.
Förster-Fromme K. et al., (2008), FEMS Microbiol Lett. 286:78-84.
Gogerty DS. et al., (2010), Appl Environ Microbiol. 76:8004-8010.
Harrington KJ. et al., (2001), Proc Natl Acad Sci USA. 98:5019-5024.
Kovach ME. et al., (1995), Gene. 166:175-176.
Lerner CG. et al., (1990), Nucleic Acids Res. 18:4631.
Liebl W. et al., (1989), ApplMicrobiol Biotechnol. 32:205-210.
Lutz R. et al., (1997), Nucleic Acids Res. 25:1203-1210.
Miller JH. el al., (1992), A Short Course in Bacterial Genetics: A Laboratory Manual and Handbook for *Escherichia coli* and Related Bacteria, Cold Spring Harbor Laboratory Press, Cold Spring Harbor, New York.
Mohsen AW. et al., (2001), Mol Genet Metab. 73:126-137.
Nagai K. et al., (1984), Nature. 309:810-812.
Norrander J. et al., (1983), Gene. 26:101-106.
Orosz A. et al., (1991), Eur J Biochem. 201:653-659.
Park JH. et al., (2011), Biotechnol Bioeng. 108:934-946.
Perham RN. et al., (1988), Methods Enzymol. 166:330-342.
Prescott L et al., (1999), "Microbiology" 4th Edition, WCB McGraw-Hill.
Riedel C. et al., (2001), J Mol Microbiol Biotechnol. 3:573-583.
Sambrook J et al., (1989)(2001), "Molecular Cloning: A Laboratory Manual" 2nd & 3rd Editions, Cold Spring Harbor Laboratory Press.
Schaefer U. et al., (1999), Anal Biochem. 270:88-96.
Sinclair DA, Dawes IW, Dickinson JR (1993), Biochem Mol Biol Int. 31:911-922.
Skinner DD, Morgenstern MR, Fedechko RW, Denoya CD (1995), J Bacteriol. 177:183-190.
Sykes PJ. et al., (1987), J Bacteriol. 169:1619-1625.
Ward DE. et al., Claiborne A (1999), J Bacteriol. 181:5433-5442.
Zhang YX, Denoya CD, Skinner DD, Fedechko RW, McArthur HA, Morgenstern MR, Davies RA, Lobo S, Reynolds KA, Hutchinson CR (1999), Microbiology. 145:2323-2334.

(Continued)

*Primary Examiner* — Kagnew H Gebreyesus
(74) *Attorney, Agent, or Firm* — Birch, Stewart, Kolasch & Birch, LLP

(57) ABSTRACT

The present invention concerns a method for the biological preparation of prenol comprising culturing a microorganism genetically modified for the bioproduction of prenol, wherein the microorganism comprises a metabolic pathway for conversion of 3-methylcrotonyl-CoA into prenol by the action of an alcohol dehydrogenase enzyme and of an aldehyde dehydrogenase enzyme.

14 Claims, 2 Drawing Sheets

(56) References Cited

OTHER PUBLICATIONS

Figure 1:
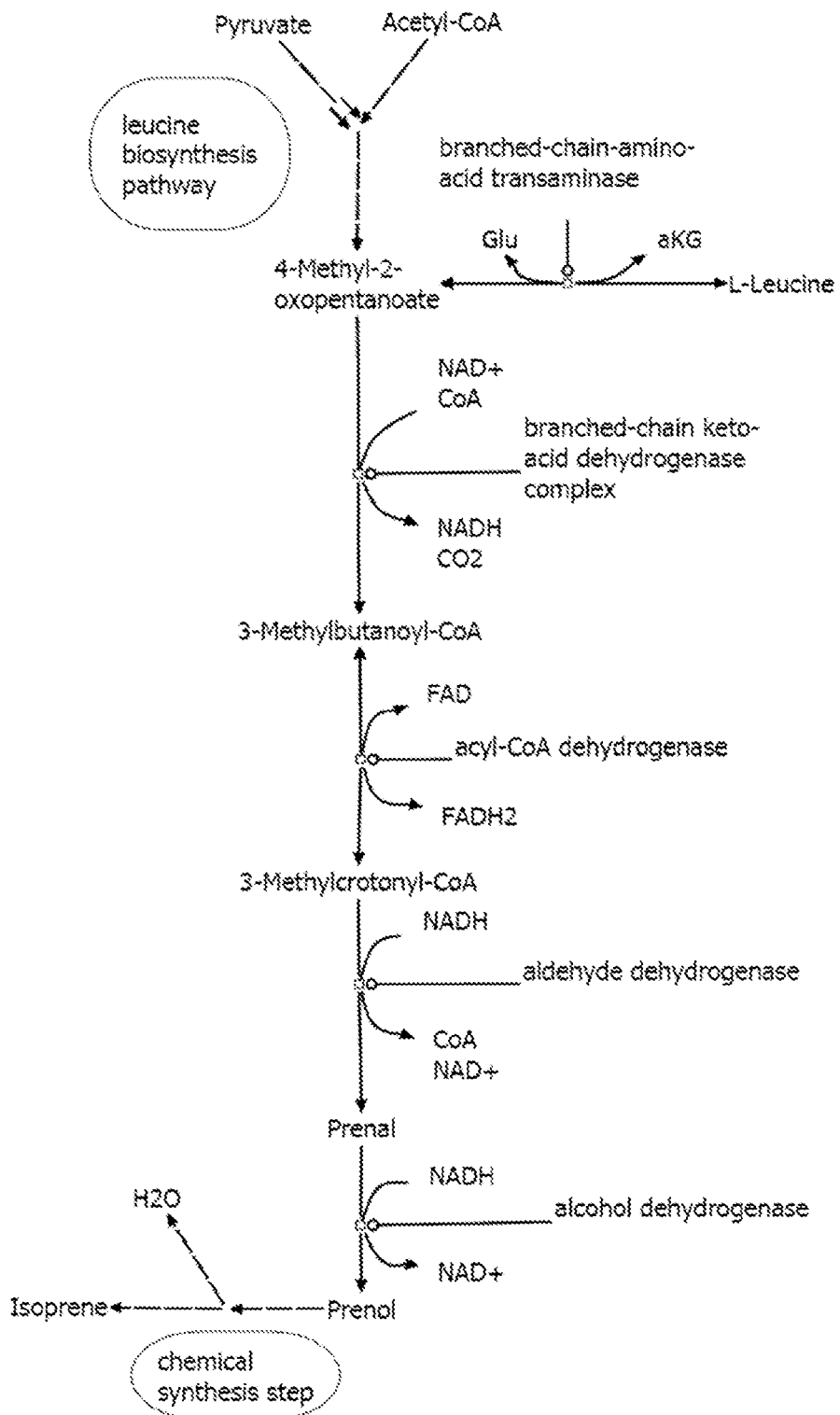

Förster-Fromme et al: "Identification of genes and proteins necessary for catabolism of acyclic terpenes and leucine/isovalerate in Pseudomonas aeruginosa", Applied and Environmental Microbiology, vol. 72, 2006, pp. 4819-4828, XP002669173.

Anderson et al: "3-methylcrotonyl-coenzyme A carboxylase is a component of the mitochondrial leucine catabolic pathway in plants", Plant Physiology, vol. 118, 1998, XP002669174.

Bode et al: "Identification of additional players in the alternative biosynthesis pathway to isovalery-CoA in the Myxobacterium Myxococcus xanthus", Chembiochem. vol. 10, 2009, pp. 128-140, XP002669181.

Lu et al: "Enhanced production of poly(3-hydroxybutyrate—co-3-hydroxyhexanoate) via manipulating the fatty acid beta-oxidation pathway in *E. coli*", FEMS Microbiology Letters, vol. 221, 2003, pp. 97-101, XP002688997.

Wallon et al: "Purification, catalytic properties and themostability of 3-isopropylmalate dehydrogenase from *Escherichia coli*", Biochimica Et Biophysica Acta, vol. 1337, 1997, pp. 105-112, XP0004281510.

European Search Report dated Feb. 9, 2012, issued in counterpart European Application No. 11 30 6313.

International Search Report dated Dec. 11, 2012, issued in counterpart International Application No. PCT/EP2012/070160.

International Search Report received in PCT/EP2012/070160 mailed Dec. 21, 2012.

Fontaine et al., "The Molecular Characterization and Transcriptional Analysis of Adhe2, The Gene Encoding The NADH-Dependent Aldehyde/Alcohol Dehydrogenase Responsible for Butanol Production in Alcohologenic Cultures of Clostridium Acetobutylicum ATCC 824," J. of Bacteriology, Feb. 2002 pp. 821-830.

Inui et al., "Expression of Clostridium acetobutylicum butanol synthetic genes in *Escherichia coli*," Appl Microbiol Biotechnol. Jan. 2008 77(6) pp. 1305-16, Epub Dec. 1, 2007.

Asanuma et al., "Molecular Characteristics and Transcription of the Gene Encoding a Multifunctional Alcohol Dehydrogenase in Relation to the Deactivation of Pyruvate Formate Lyase in the Ruminal Bacterium Streptococcus Bovis." Arch Microbiol. Feb. 2004;181(2) pp. 122-8. Epub Dec 16, 2003.

Yan et al., "Engineering metabolic systems for production of advanced fuels," J. Ind. Microbiol. Biotechnol. (2009) 36(4), pp. 471-479.

Ginger et al., The Biosynthetic Incorporation of the Intact Leucine Skeleton into Sterol by the Trypanosomatid Leishmania Mexicana, JBC, 276, 15, 2001, pp. 11674-11682.†

Fontaine et al., "The Molecular Characterization and Transcriptional Analysis of Adhe2, The Gene Encoding The NADH-Dependent Aldehyde/Alcohol Dehydrogenase Responsible for Butanol Production in Alcohologenic Cultures of Clostridium Acetobutylicum ATCC 824," J. of Bacteriology, Feb. 2002 p. 821-830.†

Inui et al., "Expression of Clostridium acetobutylicum butanol synthetic genes in *Escherichia coli*," Appl Microbiol Biotechnol. Jan. 2008 77(6) p. 1305-1316, Epub Dec.1, 2007.†

Asanuma et al., "Molecular Characteristics and Transcription of the Gene Encoding a Multifunctional Alcohol Dehydrogenase in Relation to the Deactivation of Pyruvate Formate Lyase in the Ruminal Bacterium *Streptococcus bovis*." Arch Microbiol. Feb. 2004;181(2) p. 122-128. Epub Dec 16, 2003.†

Höschle et al., "Methylcrotonyl-CoA and Geranyl-CoA Carboxylases are Involved in Leucine/Isovalerate Utilization (Liu) and Acyclic Terpene Utilization (Atu), and are Encoded by Liub/Liud and Atuc/Atuf, in Pseudomonas Aeruginosa," Microbiology, Nov. 2005;151 (Pt 11): 3649-56.†

† cited by third party

BIOSYNTHESIS PATHWAY FOR PRENOL IN A RECOMBINANT MICROORGANISM

The present invention concerns a method for the biological preparation of prenol comprising culturing a microorganism genetically modified for the bioproduction of prenol, wherein the microorganism comprises a metabolic pathway for conversion of 3-methylcrotonyl-CoA into prenol by the action of an alcohol dehydrogenase enzyme and of an aldehyde dehydrogenase enzyme.

INTRODUCTION

Prenol or 3-methyl-2-buten-1-ol (number CAS 556-82-1), has the following formula:

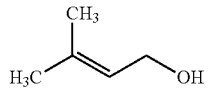

Prenol is a natural alcohol that occurs naturally in citrus fruits, cranberry, bilberry, currants, grapes, raspberry, blackberry, tomato, white bread, hop oil, coffee, arctic bramble, cloudberry and passion fruit.

Prenol is under the form of a clear, colorless oil that is reasonably soluble in water and miscible with most common organic solvents. It has a fruity odor and is used as an aroma compound, in pharmaceuticals and in perfumery. It is usually manufactured industrially, in particular by BASF.

Advantageously, prenol can be converted into isoprene, a compound of high importance for industry since it is the basis for the synthesis of synthetic rubber.

Isoprene (short for isoterpene) or 2-methyl-1,3-butadiene (Numero CAS 78-79-5) is an organic compound having the formula CH2=(CH3)CH=CH$_2$. Under standard conditions it is a colorless liquid. However, this compound is highly volatile because of its low boiling point. Isoprene is the monomer of natural rubber and also a common structure motif to an immense variety of other naturally occurring compounds, collectively termed the isoprenoids.

About 95% of isoprene production is used to produce cis-1,4-polyisoprene—a synthetic version of natural rubber. Isoprene is also copolymerized for use as a synthetic elastomer in other products such as footwear, mechanical products, medical products, sporting goods, and latex.

Isoprene was first isolated by thermal decomposition of natural rubber. It is most readily available industrially as a by-product of the thermal cracking of naphtha or oil, as a side product in the production of ethylene. While isoprene can be obtained by fractionating petroleum, the purification of this material is expensive and time-consuming.

Isoprene is naturally produced by a variety of microbial, plant, and animal species. In particular, two pathways have been identified for the biosynthesis of isoprene: the mevalonate pathway and the non-mevalonate pathway. However, the yield of isoprene from naturally-occurring organisms is commercially unattractive.

Thus, more economical methods for producing isoprene are needed. In particular, methods that produce isoprene at rates, titers, and purity that are sufficient to meet the demands of a robust commercial process are desirable. Also desired are systems for producing isoprene from inexpensive starting materials.

PRIOR ART

Although the main industrial way for producing prenol is chemical synthesis, some biosynthetic pathways have been identified recently.

The patent application WO 2009/006429 provides a method for producing prenol with a genetically modified cell expressing a first enzyme capable of catalysing the dephosphorylation of the intermediate products: isopentenyl diphosphate (IPP) or dimethylallyl diphosphate (DMAPP).

Concerning the isoprene synthesis, methods for fermentative production have been described. In particular, WO 2009/076676 describes cells comprising a heterologous nucleic acid encoding an isoprene synthase polypeptide. Two biosynthesis pathways are proposed.

The patent application WO 2010/031076 describes the conversion of prenyl derivatives, such as prenol, into isoprene. Said method comprises: a) culturing cells for producing prenol, wherein the cells comprise a heterologous isoprene synthase polypeptide, b) recovering prenol, and c) dehydrating or decarboxylating prenol to produce isoprene. The cells may further comprise: an IDI polypeptide, an MVA pathway enzyme, and a DXP pathway enzyme.

DESCRIPTION OF THE INVENTION

The present invention is related to a new biosynthesis pathway for prenol in a recombinant microorganism. This biosynthesis pathway is characterized by the intermediate product, that is 3-methylcrotonyl-CoA (number CAS 6247-62-7), and that is converted into prenol by the action of an alcohol dehydrogenase enzyme and of an aldehyde dehydrogenase enzyme.

In particular, the enzyme capable of converting 3-methylcrotonyl-CoA into prenol is the alcohol-aldehyde dehydrogenase enzyme AdhE, that is heterologous to the recombinant microorganism, and that is preferentially issued from *Clostridium acetobutylicum*.

According to the invention, the intermediate product 3-methylcrotonyl-CoA can be obtained from two different metabolic pathways:
1) From the degradation pathway of leucine, starting from a condensation of pyruvate and acetyl-CoA into 4-methyl-2-oxopentanoate, converted into 3-methylbutanoyl-CoA and then into 3-methylcrotonyl-CoA. Here, this pathway is named leucine pathway,
2) From the mevalonate biosynthesis pathway, the precursor 3-hydroxy-3-methylglutaryl-CoA being converted into 3-methylglutaconyl-CoA and then into 3-methylcrotonyl-CoA. Formation of 3-methylcrotonyl-CoA from two acetyl-CoA molecules has been suggested to be possible in the article from Gogerty and Bobik (Gogerty and Bobik, 2010). Here, this pathway is named HMG-CoA pathway.

According to a specific aspect of the invention, the obtained prenol is converted into isoprene by chemical dehydration.

DRAWINGS

FIG. 1. Metabolic pathway for biosynthesis of prenol, from the leucine pathway.

Figure 2:
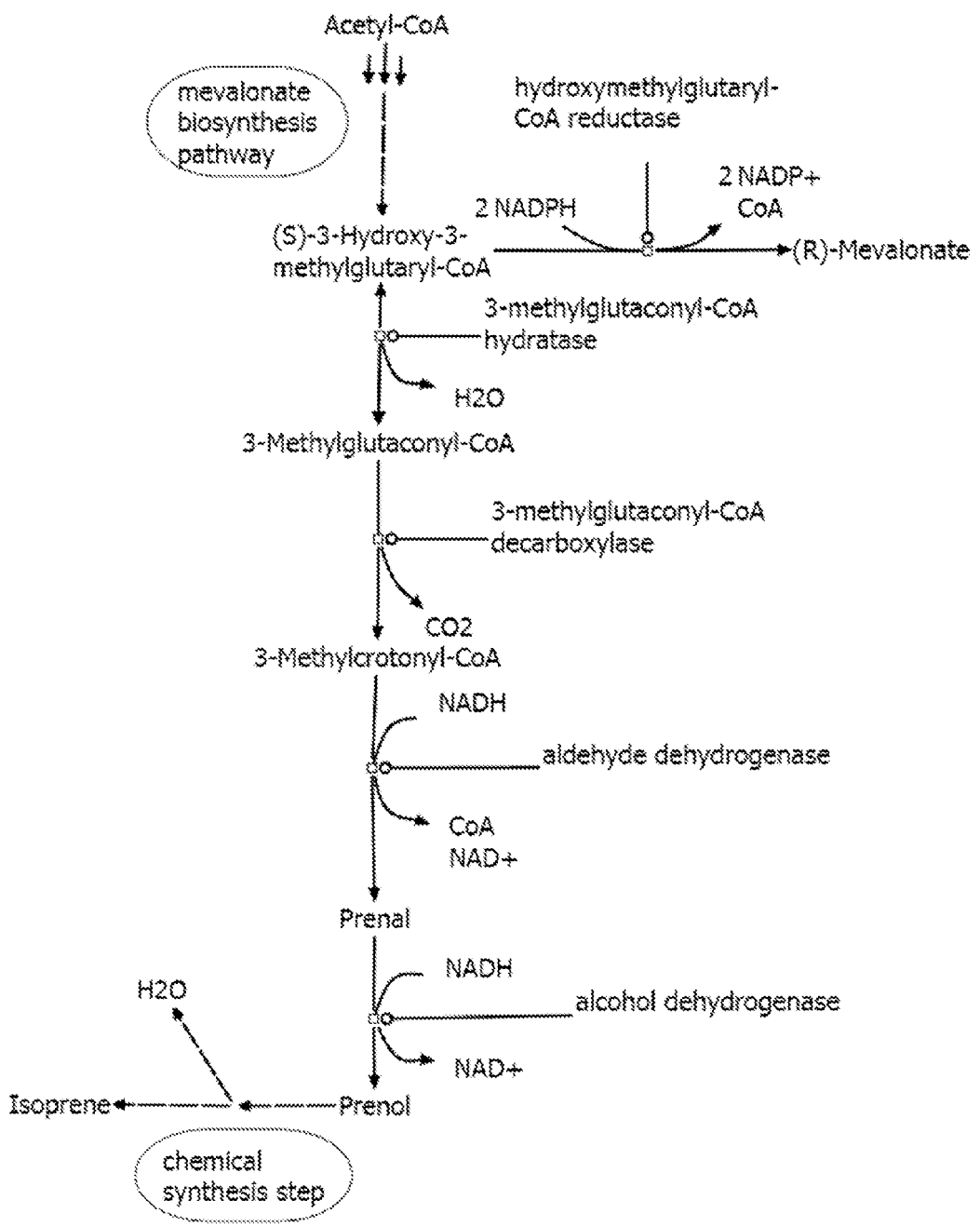

FIG. 2. Metabolic pathway for biosynthesis of prenol, from the HMG-CoA pathway.

DETAILED DESCRIPTION OF THE INVENTION

Before describing the present invention in detail, it is to be understood that this invention is not limited to particularly exemplified methods and may, of course, vary. It is also to be understood that the terminology used herein is for the purpose of describing particular embodiments of the invention only, and is not intended to be limiting, which will be limited only by the appended claims.

All publications, patents and patent applications mentioned herein are cited for the purpose of describing and disclosing the protocols, reagents and vectors that are reported in the publications and that might be used in connection with the invention.

Furthermore, the practice of the present invention employs, unless otherwise indicated, conventional microbiological and molecular biological techniques within the skill of the art. Such techniques are well known to the skilled worker, and are explained fully in the literature. See, for example, Prescott et al., (1999) and Sambrook et al., (1989) (2001).

It must be noted that as used herein and in the appended claims, the singular forms "a", "an", and "the" include plural reference unless the context clearly dictates otherwise. Thus, for example, a reference to "a microorganism" includes a plurality of such microorganisms, and a reference to "an endogenous gene" is a reference to one or more endogenous genes, and so forth. Unless defined otherwise, all technical and scientific terms used herein have the same meanings as commonly understood by one of ordinary skill in the art to which this invention belongs. Although any materials and methods similar or equivalent to those described herein can be used to practice or test the present invention, the preferred materials and methods are now described.

In the claims that follow and in the description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

DEFINITIONS

The term "prenol" as used herein refers to 3-methyl-2-buten-1-ol or to a 3,3-dimethylallyl alcohol or DMAPP-ol while the term "isoprenol" refers especially to 3-methyl-3-buten-1-ol or IPP-ol.

3-Methylcrotonyl-CoA or β-Methylcrotonyl-CoA (CAS number 6247-62-7) is an intermediate in the metabolism of leucine. It is usually formed from 3-methylbutanoyl-CoA (also called isovaleryl-coenzyme A) by isovaleryl-coenzyme A dehydrogenase.

The term "aldehyde dehydrogenase" in this invention designates the aldehyde dehydrogenase (CoA-acylating) enzyme which catalyzes the reaction of conversion of an acyl-CoA into an aldehyde.

The term "alcohol dehydrogenase" in this invention designates the enzyme which catalyzes the reaction of conversion of an aldehyde into an alcohol.

Here, the term "AdhE enzyme" refers to a bifunctional enzyme having the two activities aldehyde dehydrogenase and alcohol dehydrogenase.

The terms "activity" and "function" refer to a specific catalytic activity or function of an enzyme, i.e. the biochemical reaction(s) that is (are) catalyzed by this enzyme.

The term "microorganism", as used herein, refers to a bacterium, yeast or fungus which is not modified artificially.

The term "recombinant microorganism" or "genetically modified microorganism", as used herein, refers to a microorganism genetically modified or genetically engineered. It means, according to the usual meaning of these terms, that the microorganism of the invention is not found in nature and is modified either by introduction, by deletion or by modification of genetic elements. It can also be transformed by forcing the development and evolution of new metabolic pathways in combining directed mutagenesis and evolution under specific selection pressure (see for instance WO 2004/076659).

A microorganism may be modified to express exogenous genes if these genes are introduced into the microorganism with all the elements allowing their expression in the host microorganism. A microorganism may be modified to modulate the expression level of an endogenous gene. The modification or "transformation" of microorganisms with exogenous DNA is a routine task for those skilled in the art.

The term "endogenous gene" means that the gene was present in the microorganism before any genetic modification, in the wild-type strain. Endogenous genes may be overexpressed by introducing heterologous sequences in addition to, or to replace endogenous regulatory elements, or by introducing one or more supplementary copies of the gene into the chromosome or a plasmid. Endogenous genes may also be modified to modulate their expression and/or activity. For example, mutations may be introduced into the coding sequence to modify the gene product or heterologous sequences may be introduced in addition to or to replace endogenous regulatory elements. Modulation of an endogenous gene may result in the up-regulation and/or enhancement of the activity of the gene product, or alternatively, down regulate and/or lower the activity of the endogenous gene product. Another way to enhance expression of endogenous genes is to introduce one or more supplementary copies of the gene onto the chromosome or a plasmid.

The term "exogenous gene" means that the gene was introduced into a microorganism, by means well known by the man skilled in the art whereas this gene is not naturally occurring in the microorganism. Exogenous genes can be heterologous or not. A microorganism can express exogenous genes if these genes are introduced into the microorganism with all the elements allowing their expression in the host microorganism. Transforming microorganisms with exogenous DNA is a routine task for the man skilled in the art. Exogenous genes may be integrated into the host chromosome, or be expressed extra-chromosomally by plasmids or vectors. A variety of plasmids, which differ with respect to their origin of replication and their copy number in the cell, are all known in the art. These genes may be heterologous or homologous. The term "heterologous gene" means that the gene is derived from a species of microorganism different from the recipient microorganism that expresses it. It refers to a gene which is not naturally occurring in the microorganism.

In the present application, all genes are referenced with their common names and with references that give access to their nucleotidic sequences in the National Center for Biotechnology Information (NCBI) GenBank.

The man skilled in the art knows different means to modulate, and in particular up-regulate, the expression of endogenous genes. For example, a way to enhance expression of endogenous genes is to introduce one or more supplementary copies of the gene onto the chromosome or a plasmid.

Another way is to replace the endogenous promoter of a gene with a stronger promoter. These promoters may be homologous or heterologous. It is well within the ability of the person skilled in the art to select appropriate promoters, for example, the promoters Ptrc, Ptac, Plac or the lambda promoter cI are widely used.

Finally, the sequence of exogenous gene may be adapted for its expression in the host microorganism. Indeed, the man skilled in the art knows the notion of codon usage bias and how adapt nucleic sequence for a particular codon usage bias without modify the deduced protein.

The term 'overexpression' means in this context that the expression of a gene or an enzyme is increased compared to a non modified microorganism. Increase of expression of an enzyme is obtained by the increase of the expression of a gene encoding said enzyme.

The 'activity' of an enzyme is used interchangeably with the term 'function' and designates, in the context of the invention, the reaction that is catalyzed by the enzyme.

The terms "encoding" or "coding" refer to the process by which a polynucleotide, through the mechanisms of transcription and translation, produces an amino-acid sequence.

The gene(s) encoding the enzyme(s) can be exogenous or endogenous.

"Attenuation" of genes may be achieved by means and methods known to the man skilled in the art and contains gene deletion by homologous recombination, gene attenuation by insertion of an external element into the gene or gene expression under a weak promoter. The man skilled in the art knows a variety of promoters which exhibit different strength and which promoter to use for a weak genetic expression.

The "fermentation" is generally conducted in fermenters with an appropriate culture medium adapted to the microorganism being used, containing at least one simple carbon source, and if necessary co-substrates.

An "appropriate culture medium" designates a medium (e.g., a sterile, liquid media) comprising nutrients essential or beneficial to the maintenance and/or growth of the cell such as carbon sources or carbon substrate, nitrogen sources, for example, peptone, yeast extracts, meat extracts, malt extracts, urea, ammonium sulfate, ammonium chloride, ammonium nitrate and ammonium phosphate; phosphorus sources, for example, monopotassium phosphate or dipotassium phosphate; trace elements (e.g., metal salts), for example magnesium salts, cobalt salts and/or manganese salts; as well as growth factors such as amino acids and vitamins.

As an example of known culture media for *E. coli*, the culture medium can be of identical or similar composition to an M9 medium (Anderson, 1946), an M63 medium (Miller, 1992) or a medium such as defined by Schaefer et al., (1999).

As another example of culture medium for *C. glutamicum*, the culture medium can be of identical or similar composition to BMCG medium (Liebl et al., 1989) or to a medium such as described by Riedel et al., (2001).

Those skilled in the art are able to define the culture conditions for the microorganisms according to the invention. In particular the bacteria are fermented at a temperature between 20° C. and 55° C., preferentially between 25° C. and 40° C., and more specifically about 30° C. for *C. glutamicum* and about 37° C. for *E. coli*.

The term "carbon source" or "carbon substrate" or "source of carbon" according to the present invention denotes any source of carbon that can be used by those skilled in the art to support the normal growth of a micro-organism, including hexoses (such as glucose, galactose or lactose), pentoses, monosaccharides, oligosaccharides, disaccharides (such as sucrose, cellobiose or maltose), molasses, starch or its derivatives, hemicelluloses and combinations thereof.

Prenol Biosynthesis

The present invention is related to a method for the fermentative production of prenol, comprising culturing a recombinant microorganism in a culture medium comprising a source of carbon, wherein in said microorganism, the prenol biosynthesis pathway comprises 3-methylcrotonyl-CoA as intermediate product, that is converted into prenol by the action of an alcohol dehydrogenase enzyme and of an aldehyde dehydrogenase enzyme.

An alcohol dehydrogenase enzyme designates an enzyme catalyzing the following reactions, in one way or in the other:

an aldehyde(or a ketone)+NAD(P)H+H+ 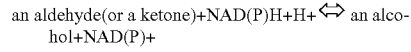 an alcohol+NAD(P)+

This enzyme always functions with an 'acceptor' of hydrogen, such as NAD+, NADP+, or other specific acceptors. The activity of this enzyme is the conversion of an alcohol into an aldehyde, and/or the conversion of an aldehyde into an alcohol with a donor of hydrogen.

Other known names are: aldehyde reductase; ADH; NAD-dependent alcohol dehydrogenase; NADH-alcohol dehydrogenase; primary alcohol dehydrogenase; aldehyde reductase (NADPH); NADP-alcohol dehydrogenase; NADP-aldehyde reductase; NADP-dependent aldehyde reductase; NADPH-aldehyde reductase; NADPH-dependent aldehyde reductase; alcohol dehydrogenase (NADP); the common abbreviation is ADH.

In a specific aspect of the invention, the enzyme having alcohol dehydrogenase activity is encoded by a gene chosen among a list of genes well known in the art, including but not limited to the genes listed in table 1:

| Gene name | Enzyme name | Organism |
|---|---|---|
| adhA | alcohol-dehydrogenase adhA from patent WO8704464-A-*Aspergillus niger* (EC: 1.1.1.1) | *A. niger* |
| ADH1 | ADH1 (ALCOHOL DEHYDROGENASE 1); alcohol dehydrogenase | *A. thaliana* |
| adhA | alcohol dehydrogenase (EC: 1.1.1.1) | *B. cereus* |
| gbsB | choline dehydrogenase (EC: 1.1.1.—) | *B. subtilis* |
| adhB | putative oxidoreductase (EC: 1.1.1.—) | *B. subtilis* |
| adhE1 | bifunctional acetaldehyde-CoA/alcohol dehydrogenase | *C. acetobutylicum* |
| adhE2 | bifunctional acetaldehyde-CoA/alcohol dehydrogenase | *C. acetobutylicum* |
| cgl2537 | putative Zn-NADPH:quinone dehydrogenase (EC: 1.1.1.1) | *C. glutamicum* |
| cgl0222 | Zn-dependent alcohol dehydrogenase (EC: 1.1.1.1) | *C. glutamicum* |
| cgl2807 | Zn-dependent alcohol dehydrogenase (EC: 1.1.1.1) | *C. glutamicum* |
| aad | bifunctional acetaldehyde-CoA/alcohol dehydrogenase (EC: 1.1.1.—1.2.1.—) | *C. kluyveri* |
| adhP | ethanol-active dehydrogenase/acetaldehyde-active reductase (EC: 1.1.1.1) | *E. coli* |
| yiaY | predicted Fe-containing alcohol dehydrogenase, Pfam00465 family | *E. coli* |
| adhE | fused acetaldehyde-CoA dehydrogenase/iron-dependent alcohol dehydrogenase/pyruvate-formate lyase deactivase (EC: 1.2.1.10 1.1.1.1) | *E. coli* |

-continued

| Gene name | Enzyme name | Organism |
|---|---|---|
| frmA | alcohol dehydrogenase class III/glutathione-dependent formaldehyde dehydrogenase (EC: 1.1.1.1 1.1.1.284) | E. coli |
| adhA | alcohol dehydrogenase | E. faecalis |
| adhE | bifunctional acetaldehyde-CoA/alcohol dehydrogenase | E. faecalis |
| adhC | alcohol dehydrogenase class III | H. influenzae |
| adhP | alcohol dehydrogenase | K. pneumoniae |
| adhE | bifunctional acetaldehyde-CoA/alcohol dehydrogenase | K. pneumoniae |
| adhE | bifunctional acetaldehyde-CoA/alcohol dehydrogenase (EC: 1.2.1.10) | L. lactis |
| adhA | alcohol dehydrogenase (EC: 1.1.1.1) | L. lactis |
| ypjA | dehydrogenase | L. lactis |
| eutG | bifunctional acetaldehyde-CoA/alcohol dehydrogenase | M. succiniciproducens |
| adhC | AdhC protein | M. succiniciproducens |
| adhB | alcohol dehydrogenase II (EC: 1.1.1.1) | P. fluorescens |
| adh | alcohol dehydrogenase, zinc-containing (EC: 1.1.1.1) | P. fluorescens |
| adhC | alcohol dehydrogenase class III | P. fluorescens |
| adhA | alcohol dehydrogenase | P. putida |
| FDH1 | Glutathione-dependent formaldehyde dehydrogenase (FDH) (FALDH) (FLD) | P. stipitis |
| SAD1 | secondary alcohol dehydrogenase (SADH1) | P. stipitis |
| SAD2 | secondary alcohol dehydrogenase (SADH2) | P. stipitis |
| ADH1 | alcohol dehydrogenase | P. stipitis |
| IFR1 | Zinc-binding oxidoreductase alcohol dehydrogenase (EC: 1.1.1.1 1.6.5.5) | P. stipitis |
| ADH2 | alcohol dehydrogenase | P. stipitis |
| ypch00392 | alcohol dehydrogenase protein (EC: 1.1.1.1) | R. etli |
| ypf00190 | putative alcohol dehydrogenase protein (EC: 1.1.1.1) | R. etli |
| adhA2 | alcohol dehydrogenase protein (EC: 1.1.1.1) | R. etli |
| ypch01140 | alcohol dehydrogenase protein (EC: 1.1.1.1) | R. etli |
| ypb00013 | iron alcohol dehydrogenase protein | R. etli |
| ypch00170 | zinc-binding oxidoreductase protein | R. etli |
| adhA1 | alcohol dehydrogenase protein (EC: 1.1.1.1) | R. etli |
| adhCch | formaldehyde dehydrogenase (glutathione)/alcohol dehydrogenase protein (EC: 1.1.1.1 1.1.1.284) | R. etli |
| ypch00995 | alcohol dehydrogenase protein (EC: 1.1.1.1) | R. etli |
| ypb00024 | putative alcohol dehydrogenase protein (EC: 1.1.1.1) | R. etli |
| ypf00099 | Zn-dependent oxidoreductase protein (EC: 1.1.1.1) | R. etli |
| ypch00832 | alcohol dehydrogenase protein (EC: 1.1.1.1) | R. etli |
| adhE | alcohol dehydrogenase protein (EC: 1.1.1.1) | R. etli |
| adhCf | formaldehyde dehydrogenase (glutathione)/alcohol dehydrogenase protein (EC: 1.1.1.1 1.1.1.284) | R. etli |
| adh | alcohol dehydrogenase (EC: 1.1.1.1) | R. eutropha |
| rplK | 50S ribosomal protein L11 (EC: 1.1.1.1) | R. eutropha |
| adhC | alcohol dehydrogenase, class III (EC: 1.1.1.284) | R. eutropha |
| adhP | alcohol dehydrogenase, Zn-dependent (EC: 1.1.1.1) | R. eutropha |
| adh | alcohol dehydrogenase (EC: 1.1.1.1) | R. opacus |
| adhP | alcohol dehydrogenase (EC: 1.1.1.1) | S. aureus |
| adhA | alcohol dehydrogenase | S. aureus |
| adhE | bifunctional acetaldehyde-CoA/alcohol dehydrogenase (EC: 1.1.1.1) | S. aureus |
| adh1 | alcohol dehydrogenase | S. aureus |
| adhC | alcohol dehydrogenase (EC: 1.1.1.1) | S. aureus |
| adhA2 | alcohol dehydrogenase | S. avermitilis |
| pteB | dehydrogenase | S. avermitilis |
| adhA1 | alcohol dehydrogenase | S. avermitilis |
| adhA6 | alcohol dehydrogenase | S. avermitilis |
| adhA3 | alcohol dehydrogenase | S. avermitilis |
| ADH4 | Adh4p (EC: 1.1.1.190 1.1.1.1) | S. cerevisiae |
| ADH2 | Adh2p (EC: 1.1.1.190 1.1.1.1) | S. cerevisiae |
| ADH3 | Adh3p (EC: 1.1.1.190 1.1.1.1) | S. cerevisiae |
| ADH5 | Adh5p (EC: 1.1.1.190 1.1.1.1) | S. cerevisiae |
| SFA1 | Bifunctional enzyme containing both alcohol dehydrogenase and glutathione-dependent formaldehyde dehydrogenase activities, functions in formaldehyde detoxification and formation of long chain and complex alcohols, regulated by Hog1p-Sko1p (EC: 1.1.1.284 1.1.1.1) | S. cerevisiae |
| ADH1 | Adh1p (EC: 1.1.1.190 1.1.1.1) | S. cerevisiae |
| adhE | bifunctional acetaldehyde-CoA/alcohol dehydrogenase (EC: 1.1.1.1 1.2.1.10) | S. enterica |
| adh2 | putative iron-containing alcohol dehydrogenase | S. enterica |
| adh3 | alcohol dehydrogenase class III | S. enterica |
| adhP | alcohol dehydrogenase | S. enterica |
| adhA | alcohol dehydrogenase | S. pneumoniae |
| adhE | bifunctional acetaldehyde-CoA/alcohol dehydrogenase (EC: 1.1.1.1) | S. pneumoniae |
| adhP | alcohol dehydrogenase (EC: 1.1.1.1) | S. pneumoniae |

| Gene name | Enzyme name | Organism |
|---|---|---|
| adhB | alcohol dehydrogenase, zinc-containing | S. pneumoniae |
| adhE | bifunctional acetaldehyde-CoA/alcohol dehydrogenase (EC: 1.1.1.1) | Y. pestis |
| adhC | alcohol dehydrogenase | Y. pestis |

According to the present invention, the alcohol dehydrogenase enzyme has specific activity for prenal or 3-methyl-2-butenal (number CAS 107-86-8), an aldehyde of formula:

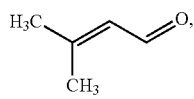

and converts it into prenol with the hydrogen donor NADH. This enzyme is also named 3-methyl-2-butenal dehydrogenase in the invention.

An aldehyde dehydrogenase (CoA-acylating) enzyme designates an enzyme catalyzing the following reaction, in one way or in the other:

an acyl-CoA+NAD(P)H+H+ ⇔ an aldehyde+ NAD++Coenzyme A

Other known names are: aldehyde:NAD+ oxidoreductase (CoA-acylating), aldehyde dehydrogenase (acylating); acylating aldehyde dehydrogenase; Coenzyme A-acylating aldehyde dehydrogenase; aldehyde dehydrogenase (acetylating); aldehyde:NAD(P)+ oxidoreductase (CoA-acetylating); the common abbreviation is ALDH.

This enzyme always functions with an 'acceptor' of hydrogen, such as NAD+, NADP+, or other specific acceptors. The activity of this enzyme is the conversion of an acyl-CoA into an aldehyde, and/or the conversion of an aldehyde into an acyl-CoA with a donor of hydrogen.

In a specific aspect of the invention, the enzyme having aldehyde dehydrogenase activity is encoded by a gene chosen among a list of genes well known in the art, including but not limited to the genes listed in table 2:

| Gene name | Enzyme name | Organism |
|---|---|---|
| eutE | acetaldehyde dehydrogenase (acetylating) (EC: 1.2.1.10) | A. hydrophila |
| mhpF | acetaldehyde dehydrogenase (EC: 1.2.1.10) | B. megaterium |
| eutE | acetaldehyde dehydrogenase (EC: 1.2.1.10) | B. megaterium |
| adhE2 | bifunctional acetaldehyde-CoA/alcohol dehydrogenase | C. acetobutylicum |
| adhE1 | bifunctional acetaldehyde-CoA/alcohol dehydrogenase | C. acetobutylicum |
| adhE | bifunctional acetaldehyde-CoA/alcohol dehydrogenase (EC: 1.2.1.10 1.1.1.1) | C. difficile |
| aad | bifunctional acetaldehyde-CoA/alcohol dehydrogenase (EC: 1.1.1.—1.2.1.—) | C. kluyveri |
| mhpF | acetaldehyde-CoA dehydrogenase II, NAD-binding (EC: 1.2.1.10) | E. coli |
| adhE | fused acetaldehyde-CoA dehydrogenase/iron-dependent alcohol dehydrogenase/pyruvate-formate lyase deactivase (EC: 1.2.1.10 1.1.1.1) | E. coli |
| adhE | bifunctional acetaldehyde-CoA/alcohol dehydrogenase | E. faecalis |
| mhpF | acetaldehyde dehydrogenase | K. pneumoniae |
| adhE | bifunctional acetaldehyde-CoA/alcohol dehydrogenase | K. pneumoniae |
| adhE | bifunctional acetaldehyde-CoA/alcohol dehydrogenase (EC: 1.2.1.10) | L. lactis |
| eutG | bifunctional acetaldehyde-CoA/alcohol dehydrogenase | M. succiniciproducens |
| mhpF | acetaldehyde dehydrogenase (EC: 1.2.1.10) | R. eutropha |
| cmtH | acetaldehyde dehydrogenase (EC: 1.2.1.10) | R. opacus |
| adhE | bifunctional acetaldehyde-CoA/alcohol dehydrogenase (EC: 1.1.1.1) | S. aureus |
| adhE | bifunctional acetaldehyde-CoA/alcohol dehydrogenase (EC: 1.1.1.1 1.2.1.10) | S. enterica |
| adhE | bifunctional acetaldehyde-CoA/alcohol dehydrogenase (EC: 1.1.1.1) | S. pneumoniae |
| adhE | metal binding site; other site (EC: 1.2.1.10) | S. typhimurium |
| adhE | bifunctional acetaldehyde-CoA/alcohol dehydrogenase (EC: 1.1.1.1) | Y. pestis |

According to the present invention, the aldehyde dehydrogenase enzyme has specific activity for 3-methylcrotonyl-CoA, an acyl-CoA of formula:

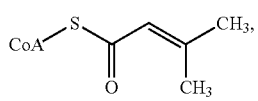

and converts it into prenal with the hydrogen donor NADH. In the invention, this enzyme is also named 3-methyl-2-butanol dehydrogenase.

In a preferred embodiment of the invention, the alcohol dehydrogenase and aldehyde dehydrogenase activities are catalyzed by the same enzyme, capable of both functions; in a specific embodiment, said enzyme capable of both functions is the alcohol-aldehyde dehydrogenase enzyme (AdhE enzyme).

Examples of enzymes possessing both activities are enzymes previously listed called "bifunctional acetaldehyde-CoA/alcohol dehydrogenase".

Preferentially, the recombinant microorganism expresses an AdhE enzyme that is heterologous to the microorganism.

According to a specific embodiment, the AdhE enzyme has specificity for the substrate 3-methylcrotonyl-CoA.

The term "specificity" designates affinity of an enzyme for a precise substrate. According to this invention specificity of AdhE enzyme means that this enzyme recognizes the 3-methylcrotonyl-CoA as preferred substrate among all other substrates.

According to a preferred embodiment of the invention, the AdhE enzyme is AdhE1 from *Clostridium acetobutylicum.*

According to a more preferred embodiment of the invention, the AdhE enzyme is encoded by the gene adhE2 from *Clostridium acetobutylicum* (listed in table 1 and table 2).

Prenol Bisosynthesis by Leucine Pathway

In this aspect of the invention, the biosynthesis pathway of 3-methylcrotonyl-CoA from pyruvate and acetyl-CoA includes the following intermediate products: 4-methyl-2-oxopentanoate and 3-methylbutanoyl-CoA.

The whole pathway for the biosynthesis of prenol according to this embodiment of the invention is illustrated in FIG. 1, entitled "Metabolic pathway for biosynthesis of prenol, from the leucine pathway".

The first reaction of the conversion of 4-methyl-2-oxopentanoate into 3-methylbutanoyl-CoA is catalysed by the branched-chain keto-acid dehydrogenase complex. This complex is composed of four subunits E1α, E1β, E2 and E3. This enzymatic complex has been identified in several species, and in particular in:

*Bacillus substilis* (genes bkdAA, bkdAB, bkdB, lpdV), for reference: Perham and Lowe, (1988).
  *Pseudomonas putida* (genes bkdA1, bkdA2, bkdB, lpdV): Sykes et al., (1987).
  *Streptomyces avermitilis*, for reference: Skinner et al., (1995).
  *Enterococcus faecalis* (operon bkdABCD), for reference: Ward et al., (1999).
  *Saccharomyces cerevisiae*, for reference: Sinclair et al., (1993).

In a specific aspect of the invention, the subunit E1 of the enzymatic complex having branched-chain keto acid dehydrogenase activity is encoded by a gene chosen among a list of genes well known in the art, including but not limited to the genes listed in table 3:

| Gene name | Enzyme name | Organism |
|---|---|---|
| bkdA2 | 2-oxoisovalerate dehydrogenase beta subunit | *A. tumefaciens* |
| bkdA1 | 2-oxoisovalerate dehydrogenase alpha subunit | *A. tumefaciens* |
| bkdA2 | 2-oxoisovalerate dehydrogenase beta subunit (EC: 1.2.4.4) | *B. brevis* |
| bkdA1 | 2-oxoisovalerate dehydrogenase alpha subunit (EC: 1.2.4.4) | *B. brevis* |
| bfmbAb | 3-methyl-2-oxobutanoate dehydrogenase, beta subunit (EC: 1.2.4.4) | *B. cereus* |
| bfmbAa | 3-methyl-2-oxobutanoate dehydrogenase, alpha subunit (EC: 1.2.4.4) | *B. cereus* |
| bkdAB | 2-oxoisovalerate dehydrogenase E1 component subunit beta (EC: 1.2.4.4) | *B. megaterium* |
| bkdAA | 2-oxoisovalerate dehydrogenase E1 component subunit alpha (EC: 1.2.4.4) | *B. megaterium* |
| bkdAA | branched-chain alpha-keto acid dehydrogenase E1 subunit (EC: 1.2.4.4) | *B. subtilis* |
| bkdAB | branched-chain alpha-keto acid dehydrogenase E1 subunit (EC: 1.2.4.4) | *B. subtilis* |
| bkdB | branched-chain alpha-keto acid dehydrogenase, E1 component, beta subunit | *E. faecalis* |
| bkdA | branched-chain alpha-keto acid dehydrogenase, E1 component, alpha subunit | *E. faecalis* |
| BCKDHA | branched chain keto acid dehydrogenase E1, alpha polypeptide (EC: 1.2.4.4) | *H. sapiens* |
| BCKDHB | branched chain keto acid dehydrogenase E1, beta polypeptide (EC: 1.2.4.4) | *H. sapiens* |
| bkdB | TPP-dependent branched-chain alpha-keto acid dehydrogenase, E1 beta subunit (branched-chain alpha-keto acid dehydrogenase, E1 component, beta subunit) | *L. casei* |
| bkdA | branched-chain alpha-keto acid dehydrogenase, E1 component, alpha subunit | *L. casei* |
| Bckdha | branched chain ketoacid dehydrogenase E1, alpha polypeptide (EC: 1.2.4.4) | *M. musculus* |
| Bckdhb | branched chain ketoacid dehydrogenase E1, beta polypeptide (EC: 1.2.4.4) | *M. musculus* |
| bkdA1 | 2-oxoisovalerate dehydrogenase (alpha subunit) | *P. aeruginosa* |
| bkdA2 | 2-oxoisovalerate dehydrogenase (beta subunit) | *P. aeruginosa* |
| bkdA2 | 2-oxoisovalerate dehydrogenase, beta subunit | *P. putida* |
| bkdA1 | 3-methyl-2-oxobutanoate dehydrogenase | *P. putida* |
| bkDa1 | 2-oxoisovalerate dehydrogenase alpha subunit protein | *R. etli* |
| bkDa2 | 2-oxoisovalerate dehydrogenase beta subunit protein | *R. etli* |
| Bckdhb | branched chain keto acid dehydrogenase E1, beta polypeptide (EC: 1.2.4.4) | *R. norvegicus* |
| Bckdha | branched chain ketoacid dehydrogenase E1, alpha polypeptide (EC: 1.2.4.4) | *R. norvegicus* |

-continued

| Gene name | Enzyme name | Organism |
| --- | --- | --- |
| bfmBAA | 2-oxoisovalerate dehydrogenase alpha subunit (EC: 1.2.4.4) | *S. aureus* |
| bfmBAB | 2-oxoisovalerate dehydrogenase beta subunit (EC: 1.2.4.4) | *S. aureus* |

In a specific aspect of the invention, the subunit E2 of the enzymatic complex having branched-chain keto acid dehydrogenase activity is encoded by a gene chosen among a list of genes well known in the art, including but not limited to the genes listed in table 4:

| Gene name | Enzyme name | Organism |
| --- | --- | --- |
| bkdB | branched-chain alpha-keto acid dehydrogenase subunit E2 | *A. tumefaciens* |
| bkdB | lipoamide acyltransferase component of branched-chain alpha-keto acid dehydrogenase complex (EC: 2.3.1.168) | *B. brevis* |
| bfmbB | branched-chain alpha-keto acid dehydrogenase subunit E2 (EC: 2.3.1.—) | *B. cereus* |
| bkdB | branched-chain alpha-keto acid dehydrogenase complex lipoamide acyltransferase E2 component (EC: 2.3.1.168) | *B. megaterium* |
| bkdB | branched-chain alpha-keto acid dehydrogenase subunit E2 (EC: 2.3.1.—) | *B. subtilis* |
| bkdC | branched-chain alpha-keto acid, E2 component, dihydrolipoamide acetyltransferase | *E. faecalis* |
| DBT | dihydrolipoamide branched chain transacylase E2 (EC: 2.3.1.168) | *H. sapiens* |
| bkdC | branched-chain alpha-keto acid, E2 component, dihydrolipoamide acetyltransferase | *L. casei* |
| Dbt | dihydrolipoamide branched chain transacylase E2 (EC: 2.3.1.168) | *M. musculus* |
| bkdB | branched-chain alpha-keto acid dehydrogenase subunit E2 | *P. aeruginosa* |
| bkdB | branched-chain alpha-keto acid dehydrogenase subunit E2 | *P. putida* |
| bkdB | branched-chain alpha-keto acid dehydrogenase subunit E2 (EC: 2.3.1.12) | *R. etli* |
| Dbt | dihydrolipoamide branched chain transacylase E2 (EC: 2.3.1.168) | *R. norvegicus* |
| bfmB | lipoamide acyltransferase component of branched-chain alpha-keto acid dehydrogenase complex (EC: 2.3.1.—) | *S. aureus* |

In a specific aspect of the invention, the subunit E3 of the enzymatic complex having branched-chain keto acid dehydrogenase activity is encoded by a gene chosen among a list of genes well known in the art, including but not limited to the genes listed in table 5:

| Gene name | Enzyme name | Organism |
| --- | --- | --- |
| lpdA | dihydrolipoamide dehydrogenase (EC: 1.8.1.4) | *A. tumefaciens* |
| pdhD | dihydrolipoyl dehydrogenase (EC: 1.8.1.4) | *B. brevis* |
| acoL | dihydrolipoamide dehydrogenase (EC: 1.8.1.4) | *B. brevis* |
| lpd | dihydrolipoamide dehydrogenase (EC: 1.8.1.4) | *B. brevis* |
| acoL | dihydrolipoamide dehydrogenase (EC: 1.8.1.4) | *B. cereus* |
| pdhD | pyruvate dehydrogenase complex E3 component, dihydrolipoamide dehydrogenase (EC: 1.8.1.4) | *B. megaterium* |
| lpdV | branched-chain alpha-keto acid dehydrogenase complex dihydrolipoamide dehydrogenase (EC: 1.8.1.4) | *B. megaterium* |
| acoL | acetoin dehydrogenase E3 component (dihydrolipoamide dehydrogenase) (EC: 1.8.1.4) | *B. megaterium* |
| pdhD | dihydrolipoamide dehydrogenase (EC: 1.8.1.4) | *B. subtilis* |
| acoL | dihydrolipoamide dehydrogenase (EC: 1.8.1.4) | *B. subtilis* |
| lpdV | dihydrolipoamide dehydrogenase (EC: 1.8.1.4) | *B. subtilis* |
| bkdD | branched-chain alpha-keto acid dehydrogenase, E3 component, dihydrolipoamide dehydrogenase | *E. faecalis* |
| lpdA | dihydrolipoamide dehydrogenase (EC: 1.8.1.4) | *E. faecalis* |
| DLD | dihydrolipoamide dehydrogenase (EC: 1.8.1.4) | *H. sapiens* |
| bkdD | dihydrolipoyl dehydrogenase (EC: 1.8.1.4) | *L. casei* |
| pdhD | dihydrolipoamide dehydrogenase (EC: 1.8.1.4) | *L. casei* |
| Dld | dihydrolipoamide dehydrogenase (EC: 1.8.1.4) | *M. musculus* |
| lpd3 | dihydrolipoamide dehydrogenase (EC: 1.8.1.4) | *P. aeruginosa* |
| lpdG | dihydrolipoamide dehydrogenase (EC: 1.8.1.4) | *P. aeruginosa* |

-continued

| Gene name | Enzyme name | Organism |
|---|---|---|
| lpdV | dihydrolipoamide dehydrogenase (EC: 1.8.1.4) | *P. aeruginosa* |
| lpdG | dihydrolipoamide dehydrogenase (EC: 1.8.1.4) | *P. putida* |
| lpd3 | dihydrolipoamide dehydrogenase (EC: 1.8.1.4) | *P. putida* |
| lpdV | dihydrolipoamide dehydrogenase (EC: 1.8.1.4) | *P. putida* |
| lpdAc | dihydrolipoamide dehydrogenase (EC: 1.8.1.4) | *R. etli* |
| lpdAch1 | dihydrolipoamide dehydrogenase (EC: 1.8.1.4) | *R. etli* |
| lpdAch2 | dihydrolipoamide dehydrogenase (EC: 1.8.1.4) | *R. etli* |
| pdhD | dihydrolipoamide dehydrogenase (EC: 1.8.1.4) | *S. aureus* |
| lpdA | dihydrolipoamide dehydrogenase (EC: 1.8.1.4) | *S. aureus* |

Preferentially, the enzymatic complex having branched-chain keto acid dehydrogenase activity is the complex from *P. putida*.

The second reaction of the conversion of 3-methylbutanoyl-CoA into 3-methylcrotonyl-CoA is catalysed by an acyl-CoA dehydrogenase, in particular an isovaleryl-CoA dehydrogenase. This enzyme has been identified in several species, and in particular in:

*Pseudomonas aeruginosa* (gene liuA), for reference: Förster-Fromme and Jendrossek (2008).

*Streptomyces coelicolor* and *Streptomyces avermitilis* (acdH), for reference: Zhang et al., (1999).

*Caenorhabditis elegans* (ivd) Mohsen et al., (2001).

*Arabidopsis thaliana* (ivd): Däschner et al., (2001).

In a specific aspect of the invention, the enzyme having acyl-CoA dehydrogenase activity is encoded by a gene chosen among a list of genes well known in the art, including but not limited to the genes listed in table 6:

| Gene name | Enzyme name | Organism |
|---|---|---|
| IBR3 | IBR3 (IBA-RESPONSE 3); acyl-CoA dehydrogenase/oxidoreductase (EC: 1.3.99.3) | *A. thaliana* |
| IVD | IVD (ISOVALERYL-CoA-DEHYDROGENASE); ATP binding/isovaleryl-CoA dehydrogenase (EC: 1.3.99.12) | *A. thaliana* |
| acd | acyl-CoA dehydrogenase | *A. tumefaciens* |
| acd | acyl-CoA dehydrogenase | *A. tumefaciens* |
| acdA | acyl-CoA dehydrogenase, short-chain specific (EC: 1.3.99.3) | *B. cereus* |
| bcd | acyl-CoA dehydrogenase (EC: 1.3.99.3) | *B. cereus* |
| acdA | acyl-CoA dehydrogenase (EC: 1.3.99.3) | *B. megaterium* |
| fadE | acyl-CoA dehydrogenase (EC: 1.3.99.3) | *B. megaterium* |
| mmgC | acyl-CoA dehydrogenase (EC: 1.3.99.3) | *B. megaterium* |
| acdh-10 | Acyl CoA DeHydrogenase | *C. elegans* |
| acdh-7 | Acyl CoA DeHydrogenase | *C. elegans* |
| acdh-8 | Acyl CoA DeHydrogenase | *C. elegans* |
| ivd-1 | IsoValeryl-CoA Dehydrogenase | *C. elegans* |
| fadE | acyl coenzyme A dehydrogenase (EC: 1.3.99.3) | *E. coli* |
| ACADM | acyl-CoA dehydrogenase, C-4 to C-12 straight chain (EC: 1.3.99.3) | *H. sapiens* |
| IVD | isovaleryl-CoA dehydrogenase (EC: 1.3.99.10) | *H. sapiens* |
| fadE1 | acyl-CoA dehydrogenase FadE1 (EC: 1.3.99.—) | *M. bovis* |
| fadE13 | acyl-CoA dehydrogenase FadE13 (EC: 1.3.99.—) | *M. bovis* |
| fadE2 | acyl-CoA dehydrogenase FadE2 (EC: 1.3.99.—) | *M. bovis* |
| fadE20 | acyl-CoA dehydrogenase FadE20 (EC: 1.3.99.—) | *M. bovis* |
| fadE23 | acyl-CoA dehydrogenase FadE23 | *M. bovis* |
| fadE4 | acyl-CoA dehydrogenase FadE4 (EC: 1.3.99.—) | *M. bovis* |
| ibd2 | isobutyryl-CoA dehydrogenase (EC: 1.3.99.10) | *M. extorquens* |
| Acadm | acyl-Coenzyme A dehydrogenase, medium chain (EC: 1.3.99.3) | *M. musculus* |
| Ivd | isovaleryl coenzyme A dehydrogenase (EC: 1.3.99.10) | *M. musculus* |
| fadE | acyl-CoA dehydrogenase (EC: 1.3.99.3) | *P. aeruginosa* |
| liuA | putative isovaleryl-CoA dehydrogenase | *P. aeruginosa* |
| acd-6 | acyl-CoA dehydrogenase family protein | *P. fluorescens* |
| fadE | acyl-CoA dehydrogenase (EC: 1.3.99.3) | *P. fluorescens* |
| fadE1 | acyl-CoA dehydrogenase family protein | *P. fluorescens* |
| fadE13 | hypothetical protein | *P. fluorescens* |
| fadE20 | acyl-CoA dehydrogenase | *P. fluorescens* |
| ivd | isovaleryl-CoA dehydrogenase (EC: 1.3.99.10) | *P. fluorescens* |
| fadE | acyl-CoA dehydrogenase (EC: 1.3.99.3) | *P. putida* |
| ivd | acyl-CoA dehydrogenase domain containing protein | *P. putida* |
| acd1 | acyl-CoA dehydrogenase protein | *R. etli* |
| acd2 | acyl-CoA dehydrogenase protein | *R. etli* |
| ivdH | isovaleryl-CoA dehydrogenase protein | *R. etli* |
| abmD | putative acyl-CoA dehydrogenase (EC: 1.3.99.—) | *R. eutropha* |
| acaD | acyl-CoA dehydrogenase (EC: 1.3.99.3) | *R. eutropha* |

-continued

| Gene name | Enzyme name | Organism |
| --- | --- | --- |
| aidB | acyl-CoA dehydrogenase, short-chain specific (AidB protein) (EC: 1.3.99.3) | R. eutropha |
| ivd1 | isovaleryl-CoA dehydrogenase (EC: 1.3.99.10) | R. eutropha |
| ivd2 | isovaleryl-CoA dehydrogenase (EC: 1.3.99.10) | R. eutropha |
| fadE15 | acyl-CoA dehydrogenase | S. avermitilis |
| fadE17 | acyl-CoA dehydrogenase | S. avermitilis |
| fadE7 | acyl-CoA dehydrogenase | S. avermitilis |
| acdH | acyl-CoA dehydrogenase | S. avermitilis |
| acdH2 | acyl-CoA dehydrogenase | S. coelicolor |
| acdH3 | acyl-CoA dehydrogenase | S. coelicolor |
| acdC | putative acyl-CoA dehydrogenase | S. enterica |
| fadE | acyl-CoA dehydrogenase (EC: 1.3.99.3) | S. enterica |
| acdA | acyl-CoA dehydrogenase (EC: 1.3.99.3) | S. erythraea |
| acdA-3 | acyl-CoA dehydrogenase (EC: 1.3.99.3) | S. erythraea |
| fadE1 | acyl-CoA dehydrogenase (EC: 1.3.99.3) | S. erythraea |
| fadE13 | acyl-CoA dehydrogenase (EC: 1.3.99.3) | S. erythraea |
| fadE21 | putative acyl-CoA dehydrogenase (EC: 1.3.99.3) | S. erythraea |
| fadE22 | putative acyl-CoA dehydrogenase | S. erythraea |
| fadE31 | putative acyl-CoA dehydrogenase (EC: 1.3.99.3) | S. erythraea |
| fadE | domain of unknown function (DUF1974); region: DUF1974; pfam09317 (EC: 1.3.99.3) | S. typhimurium |
| acdA | acyl-CoA dehydrogenase | X. oryzae |
| fadE | acyl-CoA dehydrogenase (EC: 1.3.99.3) | X. oryzae |
| fadE | acyl-CoA dehydrogenase (EC: 1.3.99.3) | Y. pestis |

In a preferred embodiment of the invention, the acyl-CoA dehydrogenase is encoded by the gene acdH from S. avermitilis.

In a specific embodiment of the invention, in the recombinant microorganism, at least one of the following enzymes is overexpressed: an acetolactate synthase, a keto-acid reductoisomerase, a dihydroxy-acid dehydratase, a 2-isopropylmalate synthase, a 2-isopropylmalate hydrolyase, a 3-isopropylmalate dehydrogenase, a branched chain keto acid dehydrogenase complex and an acyl-CoA dehydrogenase.

In a more specific aspect of the invention, in the recombinant microorganism, branched chain keto acid dehydrogenase complex and the enzyme acyl-CoA dehydrogenase, that are overexpressed in the genetically modified microorganism, are heterologous.

In particular, the branched chain keto acid dehydrogenase is encoded by one or several genes issued from Bacillus subtilis (bkdAA, bkdAB, bkdB, lpdV), Pseudomonas putida (bkdA1, bkdA2, bkdB, lpdV), Streptomyces avermitilis, Enterococcus faecalis (bkdABCD) or Saccharomyces cerevisiae.

In particular the acyl-CoA dehydrogenase is encoded by a gene from Pseudomonas aeruginosa (liuA), Streptomyces coelicolor, Streptomyces avermitilis (acdH), Caenorhabditis elegans (ivd) or Arabidopsis thaliana (ivd).

In another aspect of the invention, the microorganism is further modified to improve the availability of at least one biosynthesis intermediate chosen among pyruvate, 3-methyl-2-oxobutanoic acid and 4-methyl-2-oxopentanoate.

In order to optimize pyruvate availability, the microorganism is modified to overexpress at least one gene involved in pyruvate biosynthesis pathway, chosen among gene coding for phosphoglycerate mutase (gpmA and pgmI in E. coli or homologous gene), enolase (eno in E. coli or homologous gene) or pyruvate kinase (pykA and pykF in E. coli or homologous gene). Alternatively or in combination, at least one gene involved in pyruvate degradation pathway is attenuated. This gene is chosen among pyruvate oxidase (poxB in E. coli or homologous gene), phosphate acetyltransferase (pta in E. coli or homologous gene), acetate kinase (ackA in E. coli or homologous gene), aldehyde/alcohol dehydrogenase (adhE in E. coli or homologous gene), pyruvate dehydrogenase operon repressor (pdhR in E. coli or homologous gene) or lactate dehydrogenase (pfl, lldD, ldhA or did in E. coli or homologous gene).

In order to optimize 3-methyl-2-oxobutanoic acid availability, the microorganism is modified to overexpress at least one gene involved in the L-valine biosynthesis pathway, chosen among gene coding for acetolactate synthase (ilvI, ilvH, ilvN and ilvB in E. coli or homologous genes), keto-acid reductoisomerase (ilvC in E. coli or homologous gene) and dihydroxy-acid dehydratase (ilvD in E. coli or homologous gene). Alternatively or in combination, the gene encoding the branched chain amino acid transaminase (ilvE in E. coli or homologous gene) is deleted in the microorganism of the invention. In another embodiment of the invention, the ilvN gene is modified so as to produce an IlvN protein which is feedback deregulated. Such mutations of ilvN are disclosed in Park et al., 2011.

In order to optimize 4-methyl-2-oxopentanoate availability, the microorganism is modified to overexpress at least one gene chosen among the genes coding for 3-isopropylmalate dehydratase (leuC, leuD in E. coli or homologous genes), 3-isopropylmalate dehydrogenase (leuB in E. coli or homologous gene) or 2-isopropylmalate synthase (leuA in E. coli or homologous gene). Alternatively or in combination, the gene encoding the branched chain amino acid transaminase (ilvE in E. coli or homologous gene) is deleted in the microorganism of the invention. In another embodiment of the invention, the leuA gene is modified so as to produce a LeuA protein which is feedback deregulated. Such mutations of leuA are disclosed in patent application U.S. Pat. No. 6,403,342.

Prenol Bisosynthesis by HMG-CoA Pathway

In this aspect of the invention, the biosynthesis pathway of 3-methylcrotonyl-CoA from pyruvate and acetyl-CoA includes the following intermediate products: 3-hydroxy-3-methylglutaryl-CoA (HMG-CoA) and 3-methylglutaconyl-CoA.

The whole pathway for the biosynthesis of prenol according to this embodiment of the invention is illustrated in FIG. 2, entitled "Metabolic pathway for biosynthesis of prenol, from an intermediate of the HMG-CoA pathway".

The first reaction of condensation of two acetyl-CoA molecules into 3-hydroxy-3-methylglutaryl-CoA (HMG-CoA) is catalysed successively by two enzymes: (1) an acetyl-CoA acetyltransferase, and (2) a 3-hydroxy-3-methylglutaryl-CoA synthase.

Genes coding for enzymes having an acetyl-CoA acetyltransferase activity have been identified in several species, and in particular in *Escherichia coli* (gene atoB), *Clostridium acetobutylicum* (thlA) and *Saccharomyces cerevisiae* (ERG10).

In a specific aspect of the invention, the enzyme having acetyl-CoA acetyltransferase activity is encoded by a gene chosen among a list of genes well known in the art, including but not limited to the genes listed in table 7:

| Gene name | Enzyme name | Organism |
|---|---|---|
| ACAT2 | ACAT2 (ACETOACETYL-CoA THIOLASE 2); acetyl-CoA C-acetyltransferase/catalytic (EC: 2.3.1.9) | *A. thaliana* |
| mmgA | acetyl-CoA acetyltransferase (EC: 2.3.1.9) | *B. brevis* |
| thl | acetyl-CoA acetyltransferase | *B. cereus* |
| atoB | acetyl-CoA acetyltransferase | *B. cereus* |
| thiL | acetyl-CoA acetyltransferase (EC: 2.3.1.9) | *C. acetobutylicum* |
| ERG10 | similar to Acetoacetyl-CoA Thiolase A; mevalonate/sterol pathway | *C. albicans* |
| thlA1 | acetyl-CoA acetyltransferase (EC: 2.3.1.9) | *C. difficile* |
| thlA2 | putative acetyl-CoA acetyltransferase (EC: 2.3.1.9) | *C. difficile* |
| kat-1 | 3-Ketoacyl-CoA Thiolase | *C. elegans* |
| thlA1 | acetyl-CoA acetyltransferase (EC: 2.3.1.9) | *C. kluyveri* |
| thlA2 | acetyl-CoA acetyltransferase (EC: 2.3.1.9) | *C. kluyveri* |
| thlA3 | acetyl-CoA acetyltransferase (EC: 2.3.1.9) | *C. kluyveri* |
| atoB | acetyl-CoA acetyltransferase (EC: 2.3.1.9) | *E. coli* |
| yqeF | predicted acyltransferase | *E. coli* |
| ACAT1 | acetyl-CoA acetyltransferase 1 (EC: 2.3.1.9) | *H. sapiens* |
| ACAT2 | acetyl-CoA acetyltransferase 2 (EC: 2.3.1.9) | *H. sapiens* |
| yqeF | acetyl-CoA acetyltransferase | *K. pneumoniae* |
| thiL | acetyl coenzyme A acetyltransferase (EC: 2.3.1.9) | *L. lactis* |
| fadA | acetyl coenzyme A acetyltransferase (EC: 2.3.1.9) | *L. lactis* |
| fadA | acetyl-CoA acetyltransferase (EC: 2.3.1.9) | *M. bovis* |
| fadA6 | acetyl-CoA acetyltransferase (EC: 2.3.1.9) | *M. bovis* |
| fadA3 | acetyl-CoA acetyltransferase (EC: 2.3.1.9) | *M. bovis* |
| fadA4 | acetyl-CoA acetyltransferase (EC: 2.3.1.9) | *M. bovis* |
| fadA2 | acetyl-CoA acetyltransferase (EC: 2.3.1.9) | *M. bovis* |
| fadA5 | acetyl-CoA acetyltransferase (EC: 2.3.1.9) | *M. bovis* |
| phaA | beta-ketothiolase (EC: 2.3.1.16) | *M. dichloromethanicum* |
| Acat1 | acetyl-Coenzyme A acetyltransferase 1 (EC: 2.3.1.9) | *M. musculus* |
| Acat2 | acetyl-Coenzyme A acetyltransferase 2 (EC: 2.3.1.9) | *M. musculus* |
| atoB | acetyl-CoA acetyltransferase (EC: 2.3.1.9) | *P. aeruginosa* |
| atoB | acetyl-CoA acetyltransferase | *P. putida* |
| fadAx | acetyl-CoA acetyltransferase | *P. putida* |
| ERG10 | acetyl-CoA acetyltransferase (EC: 2.3.1.9) | *P. stipitis* |
| fadA | acetyl-CoA acetyltransferase (EC: 2.3.1.9) | *R. etli* |
| phbAch | acetyl-CoA acetyltransferase (EC: 2.3.1.9) | *R. etli* |
| phbAf | acetyl-CoA acetyltransferase (beta-ketothiolase) protein (EC: 2.3.1.9) | *R. etli* |
| phaA | acetyl-CoA acetyltransferase (EC: 2.3.1.9) | *R. eutropha* |
| bktB | beta-ketothiolase (EC: 2.3.1.9) | *R. eutropha* |
| fadA | acetyl-CoA acetyltransferase (EC: 2.3.1.16) | *R. opacus* |
| pcaF | acetyl-CoA acetyltransferase (EC: 2.3.1.174) | *R. opacus* |
| fadA5 | 3-ketoacyl-CoA thiolase/acetyl-CoA acetyltransferase | *S. avermitilis* |
| fadA1 | acetyl-CoA acetyltransferase (EC: 2.3.1.9) | *S. avermitilis* |
| fadA7 | acetyl-CoA acetyltransferase (EC: 2.3.1.9) | *S. avermitilis* |
| fadA4 | acetyl-CoA acetyltransferase (EC: 2.3.1.9) | *S. avermitilis* |
| fadA2 | acetyl-CoA acetyltransferase (EC: 2.3.1.9) | *S. avermitilis* |
| fadA3 | acetyl-CoA acetyltransferase (EC: 2.3.1.9) | *S. avermitilis* |
| ERG10 | Acetyl-CoA C-acetyltransferase (acetoacetyl-CoA thiolase), cytosolic enzyme that transfers an acetyl group from one acetyl-CoA molecule to another, forming acetoacetyl-CoA; involved in the first step in mevalonate biosynthesis (EC: 2.3.1.9) | *S. cerevisiae* |
| atoB | acetoacetyl-CoA thiolase | *X. oryzae* |
| yfcY | acetyl-CoA acetyltransferase (EC: 2.3.1.9) | *X. oryzae* |
| fadA | acetyl-CoA acetyltransferase (EC: 2.3.1.9) | *X. oryzae* |
| acat1 | acetyl-Coenzyme A acetyltransferase 1 (EC: 2.3.1.9) | *X. tropicalis* |
| acat2 | acetyl-Coenzyme A acetyltransferase 2 (EC: 2.3.1.9) | *X. tropicalis* |

In a preferred embodiment of the invention, the acetyl-CoA acetyltransferase is encoded by the gene atoB from *E. coli*.

Genes coding for enzymes having a 3-hydroxy-3-methyl-glutaryl-CoA synthase activity have been identified in several species, and in particular in *Enterococcus faecalis* (gene mvaS), and *Saccharomyces cerevisiae* (ERG13).

In a specific aspect of the invention, the enzyme having 3-hydroxy-3-methylglutaryl-CoA synthase activity is encoded by a gene chosen among a list of genes well known in the art, including but not limited to the genes listed in table 8:

The second reaction of the conversion of HMG-CoA into 3-methylcrotonyl-CoA is catalysed successively by two enzymes: (1) 3-methylglutaconyl-CoA hydratase, and (2) 3-methylglutaconyl-CoA decarboxylase.

Enzymes having a 3-methylglutaconyl-CoA hydratase activity have been identified in several species and in particular in *Galactomyces reessi* (See for reference: Dhar et al., 2002).

In a specific aspect of the invention, the enzyme having 3-methylglutaconyl-CoA hydratase activity is encoded by a gene chosen among a list of genes well known in the art, including but not limited to the genes listed in table 9:

| Gene name | Enzyme name | Organism |
|---|---|---|
| MVA1 | MVA1; acetyl-CoA C-acetyltransferase/hydroxymethylglutaryl-CoA synthase (EC: 2.3.3.10) | *A. thaliana* |
| pksG | acetyl-S-AcpK beta-ketothioester polyketide intermediate transferase | *B. subtilis* |
| HMGCS1 | 3-hydroxy-3-methylglutaryl-Coenzyme A synthase 1 (soluble) | *B. taurus* |
| HMGCS2 | 3-hydroxy-3-methylglutaryl-CoA synthase 2 (mitochondrial) (EC: 2.3.3.10) | *B. taurus* |
| ERG13 | 3-hydroxy-3-methylglutaryl coenzyme A synthase | *C. albicans* |
| HMGCS1 | 3-hydroxy-3-methylglutaryl-CoA synthase 1 (soluble) | *E. caballus* |
| mvaS | 3-hydroxy-3-methylglutaryl-CoA synthase | *E. faecalis* |
| HMGCS1 | 3-hydroxy-3-methylglutaryl-CoA synthase 1 (soluble) (EC: 2.3.3.10) | *H. sapiens* |
| HMGCS2 | 3-hydroxy-3-methylglutaryl-CoA synthase 2 (mitochondrial) (EC: 2.3.3.10) | *H. sapiens* |
| hmcM | hydroxymethylglutaryl-CoA synthase (EC: 2.3.3.10) | *L. lactis* |
| Hmgcs1 | 3-hydroxy-3-methylglutaryl-Coenzyme A synthase 1 (EC: 2.3.3.10) | *M. musculus* |
| Hmgcs2 | 3-hydroxy-3-methylglutaryl-Coenzyme A synthase 2 (EC: 2.3.3.10) | *M. musculus* |
| mvaS | 3-hydroxy-3-methylglutaryl coenzyme A synthase | *S. aureus* |
| ERG13 | 3-hydroxy-3-methylglutaryl-CoA (HMG-CoA) synthase, catalyzes the formation of HMG-CoA from acetyl-CoA and acetoacetyl-CoA; involved in the second step in mevalonate biosynthesis (EC: 2.3.3.10) | *S. cerevisiae* |
| | 3-hydroxy-3-methylglutaryl-Coenzyme A synthase | *S. avermitilis* |
| pksG | hydroxymethylglutaryl-CoA synthase (EC: 2.3.3.10) | *S. erythraea* |
| hmgcs1 | 3-hydroxy-3-methylglutaryl-Coenzyme A synthase 1 (soluble) (EC: 2.3.3.10) | *X. tropicalis* |
| pksG | putative hydroxymethylglutaryl-coenzyme A synthase | *Y. pestis* |

Preferentially the 3-hydroxy-3-methylglutaryl-CoA synthase is encoded by the gene mvaS from *Enterococcus faecalis*.

| Gene name | Enzyme name | Organism |
|---|---|---|
| mgh | 3-methylglutaconyl-CoA hydratase (EC: 4.2.1.18) | *A. baumannii* |
| fadB1 | enoyl-CoA hydratase | *A. radiobacter* |
| paaG | enoyl-CoA hydratase (EC: 4.2.1.17) | *B. multivorans* |
| AUH | AU RNA binding protein/enoyl-CoA hydratase (EC: 4.2.1.18) | *B. taurus* |
| AUH | AU RNA binding protein/enoyl-CoA hydratase | *C. familiaris* |
| paaF | methylglutaconyl-CoA hydratase (EC: 4.2.1.18) | *C. hutchinsonii* |
| auh | AU RNA binding protein/enoyl-Coenzyme A hydratase (EC: 4.2.1.18) | *D. rerio* |
| mvaA | enoyl-CoA hydratase (EC: 4.2.1.18) | *D. shibae* |
| | 3-methylglutaconyl-CoA hydratase | *G. reessi* |
| AUH | AU RNA binding protein/enoyl-CoA hydratase (EC: 4.2.1.18) | *H. sapiens* |
| caiD | enoyl-CoA hydratase/carnithine racemase (EC: 4.2.1.17) | *H. seropedicae* |
| AUH | AU RNA binding protein/enoyl-CoA hydratase | *M. mulatta* |
| Auh | AU RNA binding protein/enoyl-coenzyme A hydratase (EC: 4.2.1.18) | *M. musculus* |
| MXAN_3757 | methylglutaconyl-CoA hydratase | *M. xanthus* |
| liuC | gamma-carboxygeranoyl-CoA hydratase | *P. aeruginosa* |
| gnyH | gamma-carboxygeranoyl-CoA hydratase | *P. aeruginosa* |
| echA7 | gamma-carboxygeranoyl-CoA hydratase | *P. fluorescens* |
| AUH | AU RNA binding protein/enoyl-CoA hydratase | *P. troglodytes* |
| menB | naphthoate synthase (EC: 4.1.3.36) | *R. capsulatus* |
| Auh | AU RNA binding protein/enoyl-coenzyme A hydratase (EC: 4.2.1.18) | *R. norvegicus* |
| eccH2 | enoyl-CoA hydratase (EC: 4.2.1.17) | *S. meliloti* |

| Gene name | Enzyme name | Organism |
|---|---|---|
| fadB | probable enoyl-CoA hydratase (EC: 4.2.1.17) | S. ruber |
| auh | AU RNA binding protein/enoyl-Coenzyme A hydratase (EC: 4.2.1.18) | X. laevis |
| auh | AU RNA binding protein/enoyl-Coenzyme A hydratase (EC: 4.2.1.18) | X. tropicalis |

Preferentially the 3-methylglutaconyl-CoA hydratase is encoded by the gene MXAN_3757 from *Myxococcus xanthus*.

At least one gene coding for an enzyme having a 3-methylglutaconyl-CoA decarboxylase activity has been identified in *Myxococcus xanthus* (See for reference: Bode et al., 2009).

Preferentially the 3-methylglutaconyl-CoA decarboxylase is encoded by the genes MXAN_4264 and MXAN_4265 from *Myxococcus xanthus*, each of them coding for one subunit of the enzyme.

In a specific embodiment of the invention, in the recombinant microorganism, at least one of the following enzymes is overexpressed: an acetyl-CoA acetyltransferase, a HMG-CoA synthase, a 3-methylglutaconyl-CoA hydratase, and a 3-methylglutaconyl-CoA decarboxylase.

In another aspect of the invention, the microorganism is further modified to improve the availability of acetyl-CoA by:
  overexpressing at least one gene encoding the pyruvate dehydrogenase chosen among aceE, aceF or lpd. In a specific aspect of the invention, inactivation of pdhR coding for a repressor leads to an overexpression of aceE and aceF.
  modifying the lpd gene so as to produce a mutant, feedback deregulated Lpd enzyme. Such mutations of lpd are disclosed in patent application WO2005073364.
  attenuating at least one gene chosen among aldehyde/alcohol dehydrogenase (adhE), phosphate acetyltransferase (pta), acetate kinase (ackA) or citrate Synthase (gltA).

Preferentially, the microorganism of the invention is selected among *Enterobacteriaceae, Clostridiaceae, Bacillaceae, Streptomycetaceae, Corynebacteriaceae* and *Saccharomycetaceae*. More preferentially the microorganism is a species of *Escherichia, Clostridium, Bacillus, Klebsiella, Pantoea, Salmonella, Pseudomonas, Corynebacterium* or *Saccharomyces*.

According to a specific aspect of the invention, the microorganism is from the species *Escherichia coli, Klebsiella pneumoniae, Pseudomonas putida, Saccharomyces cerevisiae, Corynebacterium glutamicum* or *Bacillus subtilis*.

An especially preferred simple carbon source is glucose. Another preferred simple carbon source is sucrose.

In some embodiments of the invention, the culture medium comprises a carbon source being a by-product of another process using biomass as starting material, or eventually, the product of mechanical and/or chemical and/or enzymatic, and in such instance in vitro or in vivo, degradation of biomass, such as degradation of cellulose.

According to a specific aspect of the invention, the fermentative production of prenol comprises a step of isolation of the prenol from the culture medium. Recovering the prenol from the culture medium is a routine task for a man skilled in the art. It may be achieved by a number of techniques well known in the art including but not limiting to distillation, gas-stripping, pervaporation or liquid extraction. The expert in the field knows how adapt parameters of each technic dependant of the characteristics of the material to be separated.

Distillation may involve an optional component different from the culture medium in order to facilitate the isolation of prenol by forming azeotrope and notably with water. This optional component is an organic solvent such as cyclohexane, pentane, butanol, benzene, toluene, trichloroethylene, octane, diethylether or a mixture thereof.

Gas stripping is achieved with a stripping gas chosen among helium, argon, carbon dioxide, hydrogen, nitrogen or mixture thereof.

Liquid extraction is achieved with organic solvent as the hydrophobe phase such as pentane, hexane, heptane, dodecane.

Conversion of Prenol into Isoprene:

In a specific embodiment, the invention is also related to a method for the production of isoprene from prenol. Said method comprises the following successive steps:
  culturing a recombinant microorganism in a culture medium comprising a source of carbon, wherein in said microorganism, the prenol biosynthesis pathway comprises 3-methylcrotonyl-CoA as intermediate product, that is converted into prenol by the action of an alcohol dehydrogenase enzyme and of an aldehyde dehydrogenase enzyme, and
  performing a step of chemical dehydratation of the bioproduced prenol into isoprene.

This conversion of "bioproduced prenol", i.e. prenol produced from a simple source of carbon by fermentation, into isoprene can be achieved by means and methods known to the man skilled in the art. In particular, this conversion may be achieved by chemical way involving dehydrogenation and dehydration by acid catalyst (chemical dehydratation) such as disclosed in patent application US20100216958.

Another way of conversion is the enzymatic conversion of prenol by action of a prenol kinase, an isopentenyl-diphosphate delta isomerase and an isoprene synthase polypeptide such as disclosed in patent application WO2010031076. These three enzymes may be produced in a different strain than that producing prenol or in the same strain. If they are produced independently from the prenol production, the expressed enzymes or the strains expressing these enzymes can be directly mixed, partly or not, with the fermentation medium of the strain producing prenol or with the culture supernatant wherein prenol is accumulated.

In a specific aspect of the invention, the bioproduced prenol is purified before the step of chemical dehydration.

In another embodiment of the invention, isoprene is purified by standard methods well known in the art. For examples, isoprene can be recovered by gas stripping, extractive distillation with an alcohol such as ethanol, methanol, propanol, or a combination thereof, liquid extraction or solid separation (adsorption, desorption) or combination thereof.

The present invention is also related to a genetically modified microorganism for the fermentative production of prenol such as described above. Specifically, said microorganism overexpresses at least one enzyme chosen among the group consisting of: an acetolactate synthase, a keto-acid reductoisomerase, a dihydroxy-acid dehydratase, a 2-isopropylmalate synthase, a 2-isopropylmalate hydrolyase, a 3-isopropylmalate dehydrogenase, a branched chain keto acid dehydrogenase complex and an acyl-CoA dehydrogenase, an acetyl-CoA C-acetyltransferase, a HMG-CoA synthase, a 3-methylglutaconyl-CoA hydratase, and a 3-methylglutaconyl-CoA decarboxylase. In particular, the genetically modified microorganism comprises a heterologous enzyme AdhE, which has specificity for the substrate 3-methylcrotonyl-CoA.

In said genetically modified microorganism, endogenous sequences may also be knocked out or deleted, to favour the new metabolic pathway for producing prenol.

All techniques for transforming the microorganisms, and regulatory elements used for enhancing the production of prenol, are well known in the art and available in the literature, including the applicant's own patent applications on the modification of biosynthesis pathways in various microorganisms, including WO 2008/052973, WO 2008/052595, WO 2008/040387, WO 2007/144346, WO 2007/141316, WO 2007/077041, WO 2007/017710, WO 2006/082254, WO 2006/082252, WO 2005/111202, WO 2005/073364, WO 2005/047498, WO 2004/076659, the content of which is incorporated herein by reference.

EXAMPLES

The present invention is further defined in the following examples. It should be understood that these example, while indicating preferred embodiments of the invention, are given by way of illustration only. From above disclosure and these examples, the man skilled in the art can make various changes of the invention to adapt it to various uses and conditions without modifying the essentials means of the invention.

In particular, examples show modified *Escherichia coli* (*E. coli*) strains, but these modifications can easily be performed in other microorganisms of the same family.

*E. coli* belongs to the Enterobacteriaceae family, which comprises members that are Gram-negative, rod-shaped, non-spore forming and are typically 1-5 µm in length. Most members have flagella used to move about, but a few genera are non-motile. Many members of this family are a normal part of the gut flora found in the intestines of humans and other animals, while others are found in water or soil, or are parasites on a variety of different animals and plants. *E. coli* is one of the most important model organisms, but other important members of the Enterobacteriaceae family include *Klebsiella*, in particular *Klebsiella terrigena*, *Klebsiella planticola* or *Klebsiella oxytoca*, and *Salmonella*.

Protocoles

Several protocols are used to construct prenol producing strains and are described in the following examples.

Protocol 1:

Chromosomal modifications by homologous recombination and selection of recombinants (Datsenko and Wanner, 2000)

Allelic replacement or gene disruption in specified chromosomal loci is carried out by homologous recombination as described by Datsenko and Wanner (2000). The chloramphenicol (Cm) resistance cat or the kanamycin (Km) resistance kan flanked by Flp recognition sites, are amplified by PCR by using pKD3 or pKD4 plasmids as template respectively. The resulting PCR products are used to transform the recipient *E. coli* strain harbouring plasmid pKD46 that expresses the λ, Red (γ, β, exo) recombinase. Antibiotic-resistant transformants are then selected and the thermo-sensitive pKD46 plasmid is removed by cultivating the strain at 42° C. following by an isolation of the strain's culture on LB plates. Single clones are verified for the loss of ampicillin resistance and by PCR analysis with appropriate primers listed in Table 2.

The cat and kan-resistance genes are removed by using plasmid pCP20 as described by Datsenko & Wanner (2000). Antibiotic sensitive clones are then verified by PCR using primers listed in Table 2.

Protocol 2: Transduction of Phage P1

Chromosomal modifications are transferred to a given *E. coli* recipient strain by P1 transduction. The protocol is composed of 2 steps: (i) preparation of the phage lysate on a donor strain containing the resistance associated chromosomal modification and (ii) infection of the recipient strain by this phage lysate.

Preparation of the Phage Lysate

Inoculate 100 µl of an overnight culture of the strain MG1655 with the chromosomal modification of interest in 10 ml of LB+Cm 30 µg/ml or Km 50 µg/ml+glucose 0.2%+$CaCl_2$ 5 mM.

Incubate 30 min at 37° C. with shaking.

Add 100 µl of P1 phage lysate prepared on the donor strain MG1655 (approx. $1 \times 10^9$ phage/ml).

Shake at 37° C. for 3 hours until the complete lysis of cells.

Add 200 µl of chloroform, and vortex.

Centrifuge 10 min at 4500 g to eliminate cell debris.

Transfer of supernatant to a sterile tube.

Store the lysate at 4° C.

Transduction

Centrifuge 10 min at 1500 g 5 ml of an overnight culture of the *E. coli* recipient strain cultivated in LB medium.

Suspend the cell pellet in 2.5 ml of $MgSO_4$ 10 mM, $CaCl_2$ 5 mM.

Infect 100 µl cells with 100 µl P1 phage of strain MG1655 with the modification on the chromosome (test tube) and as a control tubes 100 µl cells without P1 phage and 100 µl P1 phage without cells.

Incubate 30 min at 30° C. without shaking.

Add 100 µl sodium citrate 1 M in each tube, and vortex.

Add 1 ml of LB.

Incubate 1 hour at 37° C. with shaking.

Centrifuge 3 min at 7000 rpm.

Plate on LB+Cm 30 µg/ml or Km 50 µg/ml.

Incubate at 37° C. overnight.

The antibiotic-resistant transductants are then selected and the chromosomal structure of the mutated locus was verified by PCR analysis with appropriates primers listed in Table 2.

TABLE 1

Describe the genotype and corresponding number of intermediate strains and producing strains that appear in the following examples.

| Strain number | Genotype |
|---|---|
| 1 | DH5α (pNSTLL-factorXA-adhE2ca) |
| 2 | MG1655 (pCL1920-Ptrc01/RBS01*2-ilvBN*(GMV20-22DDF)CD-TT07-Ptrc01/RBS01*2-acdHsaO1ec-TT02) (pBBR1MCS-Ptrc01-bkdA12B+lpdVpp-TT07) (pUC19-PlacIq-lacI-TT02-Ptrc01/OP01/RBS28-leuA*(G462D)BCD-TT07-Ptrc30/RBS01-adhE2ca-TT02) |
| 3 | MG1655 Ptrc30-atoB ΔpdhR lpd*(A55V) |
| 4 | MG1655 Ptrc30-atoB ΔpdhR lpd*(A55V) (pUC19-Ptrc01/OP01/RBS01-adhE2ca-RBS01*2-mvaSefO1ec-TT02) (pCL1920-Ptrc01/RBS01*2-MXANmxO1ec(3757-4264-4265)-TT07) |

1.2—Simulation Results

| | Prenol on glucose by the "leucine pathway" | Prenol on glucose by the "HMG-CoA pathway" | Prenol on sucrose by the "leucine pathway" | Prenol on sucrose by the "HMG-CoA pathway" |
|---|---|---|---|---|
| Maximum theoretical yield (g/g) | 0.32 | 0.32 | 0.34 | 0.34 |
| Maximum practical yield (g/g) | 0.24 | 0.24 | 0.26 | 0.26 |

TABLE 2

Primers used for PCR verifications of chromosomal modifications described in the following examples

| Genes name | Primers name | SEQ ID N° | Location of the homology with the chromosomal region | Sequences |
|---|---|---|---|---|
| atoB | atoB F | 17 | 2323586-2323603 | CCATCAATACCGTCAACC |
| | atoB R | 18 | 2324536-2324554 | CATAAACCTGTCCGTCTCC |
| pdhR | pdhR F | 21 | 121197-121217 | GAATGTATTTACCCACGGCAG |
| | pdhR R | 22 | 123095-123114 | GCACGCTCAACACCTTCTTC |
| lpd* (A55V) | Lpd*(A55V) ver F | 25 | 127731-127750 | GGTGGTGGTTAGGGTATTAC |
| | Lpd*(A55V) cer FR | 26 | 129415-129433 | CGTGGAGCAAGAAGACTGG |

Example 1

Calculation of Maximum Yields for Prenol Production on Glucose and Sucrose 1.1—Parameters Used for Simulations Simulations were performed with the METEX proprietary software METOPT™. A simplified metabolic network of *E. coli* was used including a central metabolic network, metabolic pathways for all biomass precursors and specific production pathways as described in FIG. 1 for the leucine pathway and FIG. 2 for the HMG-CoA pathway. A classical biomass composition for *E. coli* was used. Simulations were performed using either glucose or sucrose carbon source. For sucrose utilization, both the PTS system and the non-PTS system were modelled. As there were no differences on maximal yields calculated, only one yield on sucrose is reported. Maximum prenol yields were calculated from the "leucine pathway" and the "HMG-CoA pathway". Calculation of a theoretical maximum yield was performed, taking into account no growth and no maintenance. Calculation of a practical maximum yield was performed, taking into account a growth rate of 0.11 $h^{-1}$ and maintenance energy of 5 $mmol_{ATP} \cdot g_{DW}^{-1} \cdot h^{-1}$. All simulations were performed with a specific uptake rate of glucose of 3 $mmol \cdot g_{DW}^{-1} \cdot h^{-1}$, or a specific uptake rate of sucrose of 1.5 $mmol \cdot g_{DW}^{-1} \cdot h^{-1}$. Simulations were performed under aerobic conditions.

Example 2

Demonstration of the 3-Methyl-2-Butenal Dehydrogenase and 3-Methyl-2-Butenol Dehydrogenase Activities Encoded by the Gene adhE2 of *Clostridium acetobutylicum*

2.1—Construction of Strain DH5α (pNSTLL-Factor XA-adhE2ca)

pNSTLL-factor XA-adhE2ca plasmid was derived from pSO595 (genbank accession No AY187686) and RBS-Strep-Tag-Linker-factor XA-adhE2ca fragment with the adhE2 gene from *Clostridium acetobutylicum* ATCC-824 coding for the aldehyde/alcohol dehydrogenase.

In this plasmid, expression of the adhE2ca gene is driven by the promoter of the thiolase gene from *Clostridium acetobutylicum*. The RBS-Strep-Tag-Linker-factor XA-adhE2ca fragment was amplified by PCR with primers ST_LL_XA_adhE2ca F (SEQ ID No01) and adhE2ca R (SEQ ID No02) using *Clostridium acetobutylicum* genomic DNA. The PCR product was digested and cloned between the BamHI and SfoI sites of the pSO595. The ligation product was introduced in DH5α strain, the resulting strain DH5α (pNSTLL-factor XA-adhE2ca) is called strain 1 (table 1). The resulting plasmid was verified by DNA sequencing and called: pNSTLL-factor XA-adhE2ca.

```
ST_LL_XA_adhE2ca F
                                                    (SEQ ID No 1)
TAGGATCCatcaaaatttaggaggttagttagaatgtggtcacatcct caatttgaaaaaggtagtggtggtggtagtggtggtggtagtCCCGGG atcgaagggcgcatgaaagttacaaatcaaaaag
```

- sequence (bold upper case) for BamHI restriction site and extrabases
- sequence (underlined italic lower case) corresponding to RBS sequence
- sequence (underlined bold lower case) corresponding to Strep-tag sequence (Strep-Tag® II, IBA-GmbH)
- sequence (underlined lower case) corresponding to linker sequence (artificial sequence)
- sequence (upper case) for SmaI restriction site
- sequence (italic lower case) corresponding to factor XA sequence (Nagai and Thorgersen, 1984)
- sequence (bold lower case) homologous to the adhE gene of *Clostridium acetobutylicum* (36298-36277 (pSOL1), reference sequence on the NCBI GenBank)

```
              adhE2ca R
                                                    (SEQ ID No 2)
            TAAGTGGCGCCTTAAAATGATTTTATATAGATATCC
```

- sequence (bold upper case) for SfoI restriction site and extrabases,
- sequence (italic upper case) homologous to the adhE gene of *Clostridium acetobutylicum* (33722-33746 (pSOL1), reference sequence on the NCBI GenBank)

2.2—Overproduction of the Protein AdhE2ca Protein production was realised in a 1 L Schott bottle. The production strain was inoculated in fifteen precultures of 5 mL LB medium (Sigma 25%) with 2.5 g·L$^{-1}$ glucose. The temperature was maintained at 37° C. and agitation at 200 RPM.

Theses precultures were used to inoculate an 800 mL culture of MAC medium to an OD$_{600\ nm}$ of 0.3. The temperature of the culture was maintained at 37° C. and the agitation at 150 RPM. Ampicilin was added at concentration of 50 mg·L$^{-1}$ in preculture and culture. When the culture had reached an OD$_{600}$ of 0.8 (approximately 7 hours), the culture was centrifuged and the cell pellet conserved.

TABLE 3

MAC Medium composition.

| Compound | Concentration (g · L$^{-1}$) |
|---|---|
| Glycerol | 20.000 |
| Tryptone | 10.000 |
| NaCl | 5.000 |
| NaNO$_3$ | 0.085 |
| Yeast extract | 5.000 |
| K$_2$HPO$_4$ | 0.500 |
| FeSO$_4$·7H$_2$O | 0.050 |
| HEPES | 23.000 |
| Nitrilotriacetic acid | 0.200 |
| H$_2$SO$_4$ (96%) | Adjusted to pH 7.3 |

2.3—Purification of the Protein adhE2

All the purification steps were performed under anaerobic conditions.

Step 1: Preparation of Cell-Free Extracts

About 200 mg of *E. coli* biomass was suspended in 30 ml of 100 mM Tris HCl, 150 mM NaCl, 1 mM EDTA pH 8 and a protease inhibitor cocktail. The cell suspension was sonicated on ice (Sonics and Materials, 70 W) in a 50 ml conical tube during 8 cycles of 30 sec with 30 sec intervals. After sonication, cell debris was removed by centrifugation at 12000 g for 30 min at 4° C. The crude extract was incubated with 0.16 g/L Avidin during 30 min at 4° C. The crude extract was centrifuged at 12000 g for 5 min and filtered through a 0.45 µm filter.

Step 2: Affinity Purification

After Avidin treatment, the crude extract was loaded on a 1 ml StrepTrap HP column (GE Healthcare) equilibrated with 100 mM Tris-HCl, 150 mM NaCl, 1 mM EDTA pH8. The column was washed with 10 column volumes of the same buffer. The protein was eluted from the column with 6 column volumes of 100 mM Tris-HCl, 150 mM NaCl, 1 mM EDTA, 2.5 mM Desthiobiotin pH8. The fractions containing the protein were pooled. For the storage of the protein; the buffer was exchanged using a desalting column (Econo-Pac, Bio-Rad) against 100 mM Hepes pH7.5.

2.4—3-Methyl-2-Butenal Dehydrogenase Assay

3-Methyl-2-butenal dehydrogenase activity was assayed by measuring the initial rate of NADH oxidation under anaerobic conditions with a spectrophotometer at a wavelength of 340 nm and a constant temperature of 30° C. The reaction mixture using 2.5 mM 3-methyl-crotonyl-coA as substrate was carried out in 200 mM HEPES, 144 mM Semicarbazine buffer pH 7.5, 2 mM DTT, 0.2 mM NADH, and about 8 µg of purified enzyme (adhE2) in a final volume of 1 ml. Control assay (blank), lacking the substrate was run in parallel, and the value measured for the control is subtracted to the value measured for the assay in order to take into account the non-specific oxidation of NADH (Epsilon 340 nm=6290 M−1 cm-1).

One unit of enzyme activity was defined as the amount of enzyme that consumed 1 µmol substrate per mM under the conditions of the assay. Specific enzyme activity was expressed as units per mg of protein.

2.5—3-Methyl-2-Butenol Dehydrogenase Assay

3-Methyl-2-butenol dehydrogenase activity was assayed by measuring the initial rate of NADH oxidation under anaerobic conditions with a spectrophotometer at a wavelength of 340 nm and a constant temperature of 30° C. The reaction mixture using 5 mM 3-Methyl-2-butenal as substrate was carried out in 100 mM HEPES buffer pH 7.5, 2 mM DTT, 0.2 mM NADH, and about 12 µg of purified enzyme (adhE2) in a final volume of 1 ml. Control assay (blank), lacking the substrate was run in parallel and the value measured for the control is subtracted to the value measured for the assay in order to take into account non-specific oxidation of NADH (Epsilon 340 nm=6290 M−1 cm-1).

One unit of enzyme activity was defined as the amount of enzyme that consumed 1 µmol substrate per min under the conditions of the assay. Specific enzyme activity was expressed as units per mg of protein.

2.6—Activity of Purified Enzyme AdhE2

|  | Activity of purified enzyme (mUI/mg) |
|---|---|
| 3-Methyl-2-butenal dehydrogenase assay | 335 |
| 3-Methyl-2-butenol dehydrogenase assay | 56 |

Example 3

Construction of Strain 2 MG1655 (pCL1920-Ptrc01/
RBS01*2-ilvBN*(GMV20-22DDF)CD-TT07-
Ptrc01/RBS01*2-acdHsaO1ec-TT02)
(pBBR1MCS5-Ptrc01-bkdA12B+lpdVpp-TT07)
(pUC19-PlacIq-lacI-TT02-Ptrc01/OP01/RBS28-
leuA*(G462D)BCD-TT07-Ptrc30/RBS01-adhE2ca-
TT02)

3.1—Construction of pCL1920-Ptrc01/RBS01*2-ilvBN* (GMV20-22DDF)CD-TT07-Ptrc01/RBS01*2-acdHsaO1ec-TT02 Plasmid 3.1.1—Construction of Plasmid pCL1920-Ptrc01/RBS01*2-ilvBN*(GVM20-22DDF)CD-TT07

Plasmid pCL1920-Ptrc01/RBS01*2-ilvBN*(GVM20-22DDF)CD-TT07 is derived from plasmid pCL1920-Ptrc01/RBS01*2-ilvBN*(GVM20-22DDF)C described in patent applications EP11306306.9 and U.S. 61/544,748 to which the ilvD gene from *Escherichia coli* coding for the dihydroxy-acid dehydratase is added.

In this plasmid, expression of the ilvD gene is driven by a constitutive Ptrc promoter, the ilvD gene is expressed in the operon with ilvBN*(GVM20-22DDF)C and a transcriptional terminator is added downstream of the gene. The ilvD gene is amplified by PCR with primers ilvD F (SEQ ID No03) and ilvD R (SEQ ID No04) using pCL1920-Ptrc01/RBS01*2-ilvBN*(GVM20-22DDF)C-PilvE-ilvED-TT07 described in patent applications EP11306306.9 and US61/544,748. The PCR product is digested and cloned between the BamHI and NheI sites of the pCL1920-Ptrc01/RBS01*2-ilvBN* (GVM20-22DDF)C described in patent applications EP11306306.9 and US61/544,748. The resulting plasmid is verified by DNA sequencing and called: pCL1920-Ptrc01/RBS01*2-ilvBN*(GVM20-22DDF)CD-TT07.

ilvD F
(SEQ ID No 3)
TACTGGCTAGCatacaaaaaatgggacggc with
sequence (upper case) for NheI restriction site and extra-bases
sequence (bold lower case) homologous to the region upstream of ilvD gene (3951437-3951455, reference sequence in the MySql relational database (EcoGene.org))

ilvD R
(SEQ ID No 4)
agcaaggatccGCAGAAAGGCCCACCCGAAGG with
sequence (lower case) for BamHI restriction site and extra-bases
sequence (bold upper case) for T7Te transcriptional terminator sequence from T7 phage (Harrington et al., 2001).

3.1.2—Construction of Plasmid pCL1920-Ptrc01/RBS01*2-ilvBN*(GVM20-22DDF)CD-TT07-Ptrc01/RBS01*2-acdHsaO1ec-TT02

Plasmid pCL1920-Ptrc01/RBS01*2-ilvBN*(GVM20-22DDF)CD-TT07-Ptrc01/RBS01*2-acdHsaO1ec-TT02 is derived from pCL1920-Ptrc01/RBS01*2-ilvBN*(GVM20-22DDF)CD-TT07 described above and the synthetic gene acdH from *Streptomyces avermitilis* optimized for *Escherichia coli* described below.

Synthetic Gene acdHsaO1ec

A synthetic gene of the *Streptomyces avermitilis* acdH gene coding for the acyl-CoA dehydrogenase is synthesized by Invitrogen. The codon usage and GC content of the gene is adapted to *Escherichia coli* according to the supplier's matrix. The construct is cloned into supplier's pM vectors and verified by sequencing.

acdH gene sequence from *Streptomyces avermitilis* (AF143210) optimized for *Escherichia coli*: acdHsaO1ec contains the following sequence (SEQ ID No35):

```
atggatcatcgtctgacaccggaactggaagaactgcgtcgtaccgttga
agaatttgcacatgatgagagcaccgaaaatcggcgatttctatgaacgt
catgaatcccgtatgaaattgtgcgtgaaatgggtcgtatgggtctgtt
tggtctgccgtttccggaagaatatggtggtatgggtggtgattatctgg
cactgggtattgccctggaagaactggcacgtgagatagcagcgagcaat
taccctggaagccggtgttagcctgggtgcaatgccgattcacctgtttg
gcaccgatgcacagaaagcagaatggctgcctcgtctgtgtagcggtgaa
attctgggtgcataggtctgaccgaaccggatggtggtagtgatgccggt
gcaaccgtaccaccgcacgtctggatgaaagcaccaatgaatgggttat
taatggcaccaaatgcttcattaccaatagcggcaccgatatcaccggtc
tggttaccgttaccgcagttaccggtcgtaaacctgatggtaaaccgctg
attagcagcattattgaccgagcggtacaccgggattaccgagcagcacc
gtatagcaaagaggaggaatgcaagcgatacccgtgaactgagctagcag
atgacgtgaccggcagcaaatctgctgggtgaacagggtcgtggttatgc
acagtttctgcgtatcctggatgaaggtcgtattgcaattagcgcactgg
caacaggtctggcacagggttgtgagatgaaagcgttaaatatgcaggcg
aacgccatgcctaggtcgtaatattggtgcatatcaggcaatccagataa
aatcgcagatatggaaatgaaagcccatatggcacgcgaggaggcgtgat
gcagcaagccgtctggagccggtgaaccgttcaaaaagaagcagcaatt
gcaaaactgtatagcagtaccgagccgttgataatgcacgtgaagcaacc
cagattcatggtggttatggattatgaatgaatatccggagcacgtatgt
ggcgtgatagcaaaattctggaaattggtgaaggcaccagcgaagttcag
cgtatgctgattgcacgcgaactgggtctggtgggttaa
```

Construction of Plasmid pCL1920-Ptrc01/RBS01*2-ilvBN*(GVM20-22DDF)CD-IT07-Ptrc01/RBS01*2-acdHsaO1ec-TT02

In this plasmid, expression of the synthetic gene is driven by a constitutive Ptrc promoter and a transcriptional terminator is added downstream of the acdHsaO1ec synthetic gene. The acdHasaO1ec synthetic gene is amplified by PCR with primers Ptrc01-acdHsaO1ec F (SEQ ID No05) and Ptrc01-acdHsaO1ec R (SEQ ID No06) using the pM vector harbouring the acdHsaO1ec synthetic gene provided by the supplier. The PCR product is digested and cloned between the BamHI and XbaI sites of the plasmid pCL1920-Ptrc01/RBS01*2-ilvBN*(GVM20-22DDF)CD-TT07 described above. The resulting plasmid is verified by DNA sequencing and called pCL1920-Ptrc01/RBS01*2-ilvBN*(GVM20-22DDF)CD-TT07-Ptrc01/RBS01*2-acdHsaO1ec-TT02.

Ptrc01-acdHsaO1ec F (SEQ ID No 5)

TTCTGCGGATCCgagctgttgacaattaatcatccggctcgtataatgt gtggaa*GTCGACGTTAACCCTAGG*<u>taaggaggttataaa</u>*tggatcatcg*

*tctgacaccgg* with
- sequence (upper case) for BamHI restriction site and extrabases,
- sequence (bold lower case) for the trc promoter sequence (Amann et al., 1983 and Amann et al., 1988),
- sequence (italic upper case) for SalI, HpaI and AvrII restriction sites,
- sequence (underlined lower case) corresponding to RBS consensus sequence with a PsiI restriction site,
- sequence (italic lower case) homologous to the beginning of acdHsaO1ec synthetic gene sequence, Ptrc01-acdHsaO1ec R (SEQ ID No 6)

ggtcgactctagaAACAGATAAAACGAAAGGCCCAGTCTTTCGACTGAG

CCTTTCGTTTTATTTGATG<u>agatct</u>*TTAACCCACCAGACCCAGTTCGCG* with
- sequence (lower case) for the XbaI restriction site and extrabases,
- sequence (bold upper case) for $T_1$ transcriptional terminator sequence from the *Escherichia coli* rrnB gene (Orosz et al., 1991),
- sequence (underlined lower case) for BglII restriction site,
- sequence (italic upper case) homologous to the end of the acdHsaO1ec synthetic gene sequence.

3.2—Construction of Plasmid pBBR1MCS5-Ptrc01-bkdA12B+lpdVpp-TT07

Plasmid pBBR1MCS5-Ptrc01-bkdA12B+lpdVpp-TT07 is derived from pBBR1MCS5 (Kovach et al., 1995) and the bkdA1-bkdA2-bkdB-lpdV operon from *Pseudomonas putida* ATCC-23287 coding for the branched-chain keto-acid dehydrogenase complex.

In this plasmid, expression of the bkdA1-bkdA2-bkdB-lpdV operon is driven by a constitutive Ptrc promoter and a transcriptional terminator is added downstream of the operon. The bkdA1-bkdA2-bkdB-lpdV operon is amplified by PCR with primers RBSbkdA1 F (SEQ ID No07) and lpdV-TT07 XhoI R (SEQ ID No08) using *Pseudomoans putida* ATCC-23287 genomic DNA. The PCR product is digested and cloned between the XbaI and XhoI sites of the pBBR1MCS5. The resulting plasmid is verified by DNA sequencing and called: pBBR1MCS5-Ptrc01-bkdA12B+lpdVpp-TT07.

RBSbkdA1 F (SEQ ID No 7)

GCCGCTCTAGAACTAGT*gagctgttgacaattaatcatccggctcgtat*

*aatgtgtggaagtcgacGTTAAC*<u>caaatacccgagcgagcg</u> with
- sequence (upper case) for XbaI and SpeI restriction sites and extrabases,
- sequence (italic lower case) for the trc promoter sequence (Amann et al., 1983 and Amann et al., 1988),
- sequence (italic upper case) for the HpaI restriction site,
- sequence (underlined lower case) homologous to the region upstream of the bkdA1 gene.

lpdV-TT07 XhoI R (SEQ ID No 8)

taccgggccctcgagGCAGAAAGGCCCACCCGAAGGTGAGCCAGT<u>CAGA</u>

<u>TATGCAGGGCGTGGCCC</u> with
- sequence (lower case) for ApaI and XhoI restriction sites and extrabases,
- sequence (bold upper case) for T7Te transcriptional terminator sequence from T7 phage (Harrington et al., 2011),
- sequence (underlined upper case) homologous to the end of lpdV gene.

3.3—Construction of Plasmid pUC19-PlacIq-lacI-TT02-Ptrc01/OP01/RBS28-leuA*(G462D)BCD-TT07-Ptrc30/RBS01-adhE2ca-TT02

3.3.1—Construction of Plasmid pSCB-RBS28-leuABCD-TT07-Ptrc30

Plasmid pSCB-RBS28-leuABCD-TT07-Ptrc30 is derived from pSCB (Agilent) and the leuA-leuB-leuC-leuD operon from *Escherichia coli* coding for 2-isopropylmalate synthase, 3-isopropylmalate dehydrogenase and two 3-isopropylmalate dehydratase respectively.

The leuA-leuB-leuC-leuD operon is amplified by PCR with primers RBS28-leuA F (SEQ ID No09) and Ptrc30-TT07-leuD R (SEQ ID No10) using *E. coli* MG1655 genomic DNA. The PCR product is cloned in the pSCB (Agilent). The resulting plasmid is verified by DNA sequencing and called pSCB-RBS28-leuABCD-TT07-Ptrc30.

RBS28-leuA F (SEQ ID No 09)

TAACAATTTACGTAGCTCAGCCGGCACTAGTGAATTCattaaagaggaga aaGGTACC<u>atgagccagcaagtcattattttcg</u> with
- sequence (upper case) for SnaBI, BlpI, SpeI and EcoRI restriction sites and extrabases,
- sequence (bold lower case) corresponding to RBS sequence of the pZE12-luc (Lutz et al., 1997),
- sequence (bold upper case) for KpnI restriction site,
- sequence (underlined lower case) homologous to the beginning of leuA gene (83529-83505, reference sequence in the MySql relational database (EcoGene.org))

Ptrc30-TT07-leuD R (SEQ ID No 10)

tccttatacgtaTTCCACACAGTATACGAGCCGGATGATTAATCGTCAAC

AGCTCgggccc*GCAGAAAGGCCCACCCGAAGGTGAGCCAG*gtcgac*TTAA*

*TTCATAAACGCAGGTTGTTTTGC* with
- sequence (lower case) for SnaBI restriction site and extrabases,
- sequence (bold upper case) corresponding to modified trc promoter sequence (Amann et al., 1983 and Amann et al., 1988),
- sequence (bold lower case) for ApaI restriction site,
- sequence (upper case) for T7Te transcriptional terminator sequence from T7 phage (Harrington et al., 2011),
- sequence (underlined lower case) for SalI restriction site,
- sequence (italic upper case) homologous to the end of leuD gene (78848-78874, reference sequence in the MySql relational database (EcoGene.org))

3.3.2—Construction of Plasmid pSCB-RBS28-leuA*(G462D)BCD-TT07-Ptrc30

Plasmid pSCB-RBS28-leuA*(G462D)BCD-TT07-Ptrc30 is obtained from an oligonucleotide-directed mutagenesis on the pSCB-RBS28-leuABCD-TT07-Ptrc30 with primers leuA*(G462D) F (SEQ ID No11) and leuA*(G462D) R (SEQ ID No12) using pSCB-RBS28-leuABCD-TT07-Ptrc30 as template. The PCR product is digested with DpnI and transformed in competent cell. The resulting plasmid is verified by DNA sequencing and called pSCB-RBS28-leuA*(G462D)BCD-TT07-Ptrc30.

The mutant leuA described above confer leucine resistance in *E. coli*

```
leuA*(G462D) F
                                              (SEQ ID No 11)
ggccacggtaaagatgcgcttgAtcaggtggatatcgtcgctaactac
``` with
  base modification (upper case) to introduce the amino acid substitution,
  base modification (bold lower case) to introduce a BclI restriction site.

```
leuA*(G462D) R
                                              (SEQ ID No 12)
GTAGTTAGCGACGATATCCACCTGAtCAAGCGCATCTTTACCGTGGCC
``` with
  base modification (lower case) to introduce the amino acid substitution,
  base modification (bold upper case) to introduce a BclI restriction site.

3.3.3—Construction of Plasmid pUC19-PlacIq-lacI-TT02-Ptrc01/OP01/RBS01-adhE2ca-TT02

Plasmid pUC19-PlacIq-lacI-TT02-Ptrc01/OP01/RBS01-adhE2ca-TT02 is derived from pUC19-Ptrc01/OP01/RBS01-adhE2ca-TT02 described in patent application U.S. Ser. No. 13/169,703 and the PlacIq-lacI from pTRC99A (Amersham).

In this plasmid, expression of the lacI gene is driven by its natural promoter and a transcriptional terminator is added downstream of the gene. The PlacIq-lacI is amplified by PCR with primers PlacIq F (SEQ ID No13) and lad R (SEQ ID No14) using pTRC99A (Amersham). The PCR product is digested and cloned between the BamHI and SacI sites of the pUC19-Ptrc01/OP01/RBS01-adhE2ca-TT02 described in patent application U.S. Ser. No. 13/169,703. The resulting plasmid is verified by DNA sequencing and called: pUC19-PlacIq-lacI-TT02-Ptrc01/OP01/RBS01-adhE2ca-TT02.

```
PlacIq F (SEQ ID No13)
tcgggcccggatcccatttacgttgacaccatcgaatgg
``` with
  sequence (lower case) for ApaI and BamHI restriction sites and extrabases,
  sequence (underlined bold lower case) for the lacIq promoter sequence

```
lacI R
                                              (SEQ ID No 14)
ACTTAAGGAGCTCAACAGATAAAACGAAAGGCCCAGTCTTTCGACTGA

GCCTTTCGTTTTATTTGATGTACGTCACTGCCCGCTTTCCAGTCGGG
``` with
  sequence (upper case) for SacI restriction site and extrabases,
  sequence (underlined bold upper case) for T₁ transcriptional terminator sequence from the *Escherichia coli* rrnB gene (Orosz et al., 1991),
  sequence (italic upper case) homologous to the end of the lad gene.

3.3.4—Construction of Plasmid pUC19-PlacIq-lacI-TT02-Ptrc01/OP01/RBS28-leuA*(G462D)BCD-TT07-Ptrc30/RBS01-adhE2ca-TT02

Plasmid pUC19-PlacIq-lacI-TT02-Ptrc01/OP01/RBS28-leuA*(G462D)-TT07-Ptrc30/RBS01-adhE2ca-TT02 is derived from pSCB-RBS28-leuA*(G462D)BCD-TT07-Ptrc30 and pUC19-PlacIq-lacI-TT02-Ptrc01/OP01/RBS01-adhE2ca-TT02 described above.

In this plasmid, expression of the leucine operon is driven by an IPTG-inductible Ptrc promoter and expression of the adhE2ca gene is driven by a constitutive Ptrc promoter. A transcriptional terminator is added downstream the leucine operon. The pSCB-RBS28-leuA*(G462D)BCD-TT07-Ptrc30 is digested and cloned in the SnaBI site of the pUC19-PlacIq-lacI-TT02-Ptrc01/OP01/RBS01-adhE2ca-TT02. The resulting plasmid is verified by DNA sequencing and called: pUC19-PlacIq-lacI-TT02-Ptrc01/OP01/RBS28-leuA*(G462D)BCD-TT07-Ptrc30/RBS01-adhE2ca-TT02.

3.4—Construction of the Strain 2: MG1655 (pCL1920-Ptrc01/RBS01*2-ilvBN*(GMV20-22DDF)CD-TT07-Ptrc01/RBS01*2-acdHsaO1ec-TT02) (pBBR1MCS5-Ptrc01-bkdA12B+lpdVpp-TT07) (pUC19-PlacIq-lacI-TT02-Ptrc01/OP01/RBS28-leuA*(G462D)BCD-TT07-Ptrc30/RBS01-adhE2ca-TT02)

Construction of a strain with increased prenol pathway flux express the ilvBN*(GMV20-22DDF)CD operon to produce 3-methyl-2-oxobutanoic acid, the leuA*(G462D)BCD operon to produce 4-methyl-2-oxopentanoate, the bkdA12B+lpdV operon from *Pseudomonas putida* to produce 3-methylbutanoyl-CoA, the optimized acdH gene from *Streptomyces avermitilis* to produce 3-methylcrotonyl-CoA and the adhE2ca gene from *Clostridium acetobutylicum* to produce prenol.

The pCL1920-Ptrc01/RBS01*2-ilvBN*(GMV20-22DDF)CD-TT07-Ptrc01/RBS01*2-acdHsaO1ec-TT02, pBBR1MCS5-Ptrc01-bkdA12B+lpdVpp-TT07 and pUC19-PlacIq-lacI-TT02-Ptre01/OP01/RBS28-leuA*(G462D) BCD-TT07-Ptrc30/RBS01-adhE2ca-TT02 plasmids are introduced by electroporation into the MG1655 strain. The presence of the three plasmids is verified and the resulting strain MG1655 (pCL1920-Ptrc01/RBS01*2-ilvBN*(GMV20-22DDF)CD-TT07-Ptrc01/RBS01*2-acdHsaO1ec-TT02) (pBBR1MCS5-Ptrc01-bkdA12B+lpd-Vpp-TT07) (pUC19-PlacIq-lacI-TT02-Ptrc01/OP01/RBS28-leuA*(G462D)BCD-TT07-Ptrc30/RBS01-adhE2ca-TT02) is called strain 2 (Table 1).

Example 4

Construction of Strain 4: MG1655 Ptrc30-atoB ΔpdhR lpd*(A55V) (pUC19-Ptrc01/OP01/RBS01-adhE2ca-RBS01*2-mvaSefO1ec-TT02) (pCL1920-Ptrc01/RBS01*2-MXANmxO1ec(3757-4264-4265)-TT07)

4.1—Construction of the Strain 3: MG1655 Ptrc30-atoB ΔpdhR lpd*(A55V)

4.1.1—Construction of Strain MG1655 Ptrc30-atoB:Cm

To increase the expression level of acetyl-CoA acetyltransferase atoB, a constitutive artificial trc promoter is added upstream atoB gene into the strain MG1655 pKD46 according to Protocol 1, except that primers Ptrc01/OP01-atoB F (SEQ ID No15) and Ptrc30-atoB R (SEQ ID No16) are used to amplify the chloramphenicol resistance cassette from pKD3 plasmid.

Chloramphenicol resistant recombinants are selected. The presence of the artificial promoter Ptrc30 and the insertion of the resistance cassette are verified by PCR with primers atoB F (SEQ ID No17) and atoB R (SEQ ID No18) (Table 2) and by DNA sequencing. The resulting strain is called MG1655 Ptrc30-atoB:Cm.

Ptrc01/OP01-atoB F
(SEQ ID No 15)
GCATCACTGCCCTGCTCTTCTCCGGTGTCATTTTCGTCATTGGTTTAA

CGCTGTTCTGACGGCACCCCTACAAACAGAAGGAATATAAACTGGCTC

ACCTTCGGGTGGGCCTTTCTGCTGTAGGCTGGAGCTGCTTC with
sequence (upper case) homologous to sequence upstream of the atoB gene (2324042-2324130 reference sequence in the MySql relational database (EcoGene.org))
sequence (underlined upper case) for T7Te transcriptional terminator sequence from phage T7 (Harrington et al., 2001)
sequence (italic upper case) corresponding to the primer site 2 of plasmid pKD3 (Datsenko and Wanner, 2000)

Ptrc30-atoB R
(SEQ ID No 16)
CCGATAGCAGTACGTACCGCACTGACGATGACACAATTTTTCATT_TAT_

_AACCTCCTT_ATTCCACACAGTATACGAGCCGGATGATTAATCGTCAAC

AGCTCCATGGTCcatatgaatatcctccttag with
sequence (bold upper case) homologous to sequence of the atoB gene (2324131-2324174, reference sequence in the MySql relational database (EcoGene.org))
sequence (italic upper case) corresponding to RBS consensus sequence with a PsiI restriction site,
sequence (underlined upper case) for the trc promoter sequence (Amann et al., 1983 and Amann et al., 1988),
sequence (lower case) corresponding to the primer site 1 of plasmid pKD3 (Datsenko and Wanner, 2000).

4.1.2—Construction of Strain MG1655 ΔpdhR:Km

To delete the pdhR gene, which encodes a pyruvate dehydrogenase operon repressor, into the strain MG1655 pKD46, Protocol 1 is used except that primers DpdhR F (SEQ ID No19) and DpdhR R (SEQ ID No20) are used to amplify the kanamycin resistance cassette from pKD4 plasmid.

DpdhR R
(SEQ ID No 20)
gaccaattgacttcggcaagtggcttaagacaggaactcatg_attc_

_cggggatccgtcgacctgcagttcgaagttcctattctcta_gaaag tataggaacttcttcaagatccctcacgctgccgc with
sequence (lower case) homologous to sequence of pdhR gene (122053-122094, reference sequence in the MySql relational database (EcoGene.org)),
sequence (italic lower case) corresponding to the upstream region of pKD13-Km gene (Datsenko and Wanner, 2000),
sequence (bold lower case) corresponding to the FRT site and downstream region of pKD4 plasmid (Datsenko and Wanner, 2000), DpdhR F
(SEQ ID N° 19)
CATCTTCTGGATAATTTTTACCAGAAAAATCACTAATTCTTTCGTTGCT

CCAGTGTAGGCTGGAGCTGCTTCGAAGTTCCTATACTTTCTAGAGAATA

GGAACTTCAGAGCGCTTTTGAAGCTGGGG sequence (upper case) homologous to sequence of pdhR gene (122839-122888, reference sequence in the MySql relational database (EcoGene.org)),
sequence (italic upper case) corresponding to the downstream region of pKD13-Km gene (Datsenko and Wanner, 2000),
sequence (bold upper case) corresponding to the FRT site and upstream region of pKD4 plasmid (Datsenko and Wanner, 2000).

Kanamycin resistant recombinants are selected. The insertion of the resistance cassette is then verified by PCR with primers pdhR F (SEQ ID No21) and pdhR R (SEQ ID No22) (Table 2) and by DNA sequencing. The verified and selected strain is called MG1655 ΔpdhR:Km.

4.1.3—Construction of Strain MG1655 Ptrc30-atoB ΔpdhR:Km

The ΔpdhR:Km chromosomal modification is transduced into the strain MG1655 Ptrc30-atoB:Cm with a P1 phage lysate from strain MG1655 ΔpdhR:Km described above, according to Protocol 2.

Kanamycin resistant transductants are selected and the presence of ΔpdhR:Km chromosomal modification was verified by PCR with primers pdhR F (SEQ ID No21) and pdhR R (SEQ ID No22) (Table 2). The resulting strain is called MG1655 Ptrc30-atoB:Cm ΔpdhR:Km.

The kanamycin and chloramphenicol resistances of the above strain are removed according to Protocol 1. The loss of the kanamycin and chloramphenicol resistant cassettes is verified by PCR by using the primers pdhR F (SEQ ID No21) and pdhR R (SEQ ID No22) and atoB F (SEQ ID No17) and atoB R (SEQ ID No18) respectively (Table 2). The resulting strain is called MG1655 Ptrc30-atoB ΔpdhR.

4.1.4—Construction of Strain MG1655 lpd*(A55V):Km

To transfer the lpd*(A55V) mutation (described in WO2005073364 patent application), into the strain MG1655 Ptrc30-atoB ΔpdhR, a kanamycin resistant cassette is inserted downstream of the lpd*(A55V) gene according to Protocol 1 except that primers lpd*(A55V)_Cm F (SEQ ID No23) and lpd*(A55V)_Cm R (SEQ ID No24) are used to amplify the kanamycin resistance cassette from pKD4 plasmid.

Lpd*(A55V)_Cm F
(SEQ ID N° 23)
cccgaaagcgaagaagaagtaattttttcgtttgccggaacatccggca attaaaaaagcggctaaccacgccgcttttttttacgtctgcaagtgta ggctggagctgcttcg with:
sequence (lower case) homologous to sequence downstream of the lpd*(A55V) gene (129315-129405 reference sequence in the MySql relational database (EcoGene.org)), sequence (bold lower case) corresponding to the primer site 2 of plasmid pKD4 (Datsenko and Wanner, 2000), Lpd*(A55V)_Cm R
(SEQ ID N° 24)
CCATACTGTCAGGCTGAATAACGAGCAACGGTCAGCAGTATGCGAACG
TCTCTCTGAACGTGGAGCAAGAAGACTGGAAAGGTAAACATATGAATA
TCCTCCTTAG with:
- sequence (upper case) homologous to sequence downstream of the lpd*(A55V) gene (129491-129406 reference sequence in the MySql relational database (EcoGene.org)),
- sequence (bold upper case) corresponding to the primer site 1 of plasmid pKD4 (Datsenko and Wanner, 2000).

Kanamycin resistant recombinants are selected. The insertion of the resistance cassette is then verified by PCR with primers Lpd*(A55V) ver F (SEQ ID No25) and Lpd*(A55V) ver R (SEQ ID No26) and by DNA sequencing. The verified and selected strain is called MG1655 lpd*(A55V):Km.

4.1.5—Construction of Strain MG1655 Ptrc30 ΔpdhR lpd*(A55V):Km

The lpd*(A55V) chromosomal modification is transduced into the strain MG1655 Ptrc30-atoB ΔpdhR with a P1 phage lysate from strain MG1655 lpd*(A55V):Km described above, according to Protocol 2.

Kanamycin resistant transductants are selected and the presence of lpd*(A55V):Km chromosomal modification was verified by PCR with primers Lpd*(A55V) ver F (SEQ ID No25) and Lpd*(A55V) ver R (SEQ ID No26) (Table 2). The resulting strain is called MG1655 Ptrc30-atoB ΔpdhR lpd*(A55V):Km.

The kanamycin resistance of the above strain is removed according to Protocol 1. The loss of the kanamycin resistant cassette is verified by PCR using the primers Lpd*(A55V) ver F (SEQ ID No25) and Lpd*(A55V) ver R (SEQ ID No26) (Table 2). The resulting strain MG1655 Ptrc30-atoB ΔpdhR lpd*(A55V) is called strain 3 (Table 1).

4.2—Construction of pUC19-Ptrc01/OP01/RBS01-adhE2ca-RBS01*2-mvaSefO1ec-TT02 Plasmid The pUC19-Ptrc01/OP01/RBS01-adhE2ca-RBS01*2-mvaSefO1ec-TT02 plasmid is derived from pUC19 plasmid (Norrander et al., 1983), adhE2 gene from *Clostridium acetobutylicum* coding for the bifunctional aldehyde/alcohol dehydrogenase described in patent application U.S. Ser. No. 13/169,703 and the synthetic gene mvaS from *Enterococcus faecalis* coding for an hydroxymethylglutaryl-CoA synthase optimized for *Escherichia coli* described below.

In this plasmid, expressions of both genes are driven by a constitutive trc promoter with an operator site, and a transcriptional terminator is added downstream the entire construct.

Synthetic Gene mvaSefO1ec

A synthetic gene of the *Enterococcus faecalis* mvaS gene coding for an 3-hydroxy-3-methylglutaryl-CoA synthase is synthesized by Invitrogen. The codon usage and GC content of the gene is adapted to *Escherichia coli* according to the supplier's matrix. The construct is cloned into supplier's pM vectors and verified by sequencing.

mvaS gene sequence from *Enterococcus faecalis* (AF290092) optimized for *Escherichia coli*: mvaSefO1ec contains the following sequence (SEQ ID No36):

ATGACCATTGGCATCGACAAAATCAGCTTTTTTGTTCCGCCTTACTAT
ATCGACATGACCGCACTGGCCGAAGCACGTAATGTTGATCCGGGTAAA
TTTCATATTGGTATTGGTCAGGATCAGATGGCCGTTAATCCGATTAGC
CAGGATATTGTTACCTTTGCAGCAAATGCAGCAGAAGCAATTCTGACC
AAAGAAGATAAAGAAGCCATCGATATGGTTATTGTTGGCACCGAAAGC
AGCATTGATGAAAGCAAAGCAGCCGCAGTTGTTCTGCATCGTCTGATG
GGTATTCAGCCGTTTGCACGTAGCTTTGAAATTAAAGAAGCATGTTAC
GGCGCAACCGCAGGTCTGCAGCTGGCAAAAAATCATGTTGCACTGCAT
CCGGATAAAAAAGTTCTGGTTGTTGCAGCAGATATCGCCAAATATGGT
CTGAATAGCGGTGGTGAACCGACCCAGGGTGCCGGTGCAGTTGCAATG
CTGGTTGCAAGCGAACCGCGTATTCTGGCACTGAAAGAGGATAATGTT
ATGCTGACGCAGGATATCTATGATTTTTGGCGTCCGACCGGTCATCCG
TATCCGATGGTTGATGGTCCGCTGAGCAATGAAACCTATATTCAGAGC
TTTGCACAGGTGTGGGATGAACATAAAAAACGTACCGGTCTGGATTTC
GCAGATTATGATGCACTGGCCTTTCATATTCCGTACACCAAAATGGGT
AAAAAAGCACTGCTGGCCAAAATTAGCGATCAGACCGAAGCCGAACAA
GAACGTATCCTGGCACGTTATGAAGAAGCATTATCTATAGCCGTCGT
GTGGGTAATCTGTACACCGGTAGCCTGTATCTGGGTCTGATTAGCCTG
CTGGAAAATGCAACCACCCTGACCGCTGGTAATCAGATTGGTCTGTTT
AGCTATGGTAGCGGTGCCGTTGCAGAATTTTTCACAGGTGAACTGGTT
GCAGGTTATCAGAATCATCTGCAGAAAGAAACCCATCTGGCCCTGCTG
GATAATCGTACCGAACTGAGCATTGCAGAATATGAAGCAATGTTTGCA
GAAACCCTGGATACCGATATTGATCAGACCCTGGAAGATGAACTGAAA
TATAGCATTAGCGCCATTAATAACACCGTGCGTAGCTATCGTAACTAA

The mvaSefO1ec synthetic gene is amplified by PCR with primers RBS01*2-mvaSefO1ec-XhaI F (SEQ ID No27) and mvaSefO1ec-NheI R (SEQ ID No28) using the pM vector harbouring the mvaSefO1ec synthetic gene providing by the supplier. The PCR product is digested and cloned between the XbaI and NheI sites of the pUC19-Ptrc01/OP01/RBS01-adhE2ca-TT02 described in patent application U.S. Ser. No. 13/169,703. The resulting plasmid is verified by DNA sequencing and called pUC19-Ptrc01/OP01/RBS01-adhE2ca-RBS01*2-mvaSefO1ec-TT02.

RBS01*2-mvaSefO1ec-XhaI F
(SEQ ID N° 27)
gctctagaTAAGGAGGTTATAAatgaccattggcatcgac with
- sequence (lower case) for XbaI restriction site and extrabases,
- sequence (upper case) for the RBS consensus sequence with PsiI restriction site,
- sequence (underlined lower case) homologous to the beginning of mvaSefO1ec synthetic gene sequence, mvaSefO1ec-NheI R
(SEQ ID N° 28)
CTAGCTAGCTTAGTTACGATAGCTACGCAC sequence (underlined upper case) for NheI restriction site and extrabases,
sequence (upper case) homologous to the end of the mvaSefO1ec synthetic gene sequence.

4.3—Construction of pCL1920-Ptrc01/RBS01*2-MXANmxO1ec(3757-4264-4265)-TT07 Plasmid The pCL1920-Ptrc01/RBS01*2-MXANmxO1ec(3457-4264-4265)-TT07 plasmid is derived from plasmid pCL1920 (Lerner and Inouye, 1990), MXAN_3757, MXAN_4264 and MXAN_4265 synthetic genes from *Myxococcus Xanthus*, strain DK 1622, coding for a 3-methylglutaconyl-CoA hydratase, a 3-methylglutaconyl-CoA decarboxylase subunit A and B respectively, optimized for *Escherichia coli* described below.

In this plasmid, these genes are organized in operon and their expressions are driven by a constitutive trc promoter with an operator site, and a transcriptional terminator is added downstream the entire construct.

4.3.1—Construction of pCL1920-Ptrc01/RBS01*2-MXAN_3757mxO1ec Plasmid

MXAN_3757mxO1ec Synthetic Gene

A synthetic gene of the *Myxococcus xanthus* MXAN_3757 gene coding for a 3-methylglutaconyl-CoA hydratase is synthesized by Invitrogen. The codon usage and GC content of the gene is adapted to *Escherichia coli* according to the supplier's matrix. The construct is cloned into supplier's pM vectors and verified by sequencing.

MXAN_3757 gene sequence from *Myxococcus xanthus* (NC_008095) optimized for *Escherichia coli*: MXAN_3757mxO1ec contains the following sequence (SEQ ID No37):

ATGCCTGAGTTTAAAGTTGATGCACGTGGTCCGATTGAAATTTGGAC

CATTGATGGTGAAAGCCGTCGTAATGCAATTAGCCGTGCAATGCTGA

AAGAACTGGGTGAACTGGTTACCCGTGTTAGCAGCAGCCGTGATGTT

CGTGCAGTTGTTATTACCGGTGCCGGTGATAAAGCATTTTGTGCCGG

TGCCGATCTGAAAGAACGTGCAACAATGGCCGAAGATGAAGTTCGTG

CATTTCTGGATGGTCTGCGTCGTACCTTTCGTGCAATTGAAAAAAGC

GATTGCGTTTTTATTGCCGCAATTAATGGTGCAGCACTGGGTGGTGG

CACCGAACTGGCACTGGCATGTGATCTGCGTGTTGCAGCACCGGCAG

CGGAACTGGGTCTGACCGAAGTTAAACTGGGCATTATTCCGGGTGGT

GGTGGTACACAGCGTCTGGCACGTCTGGTTGGTCCGGGTCGTGCAAA

AGATCTGATTCTGACCGCACGTCGTATTAATGCAGCAGAAGCATTTA

GCGTTGGTCTGGCAAATCGCCTGGCACCGGAAGGTCATCTGCTGGCA

GTTGCCTATGGTCTGGCCGAAAGCGTTGTTGAAAATGCACCGATTGC

AGTTGCAACCGCCAAACATGCAATTGATGAAGGCACCGGTCTGGAAC

TGGATGATGCACTGGCCCTGGAACTGCGTAAATATGAAGAAATTCTG

AAAACCGAAGATCGCCTGGAAGGCCTGCGTGCATTTGCAGAAAAACG

TGCACCGGTGTATAAAGGTCGTTAA

The MXAN_3757mxO1ec synthetic gene is amplified by PCR with primers Ptrc01/RBS01*2-MXAN_3757mxO1ec-SacI F (SEQ ID No29) and MXAN_3757 mxO1ec-KpnI R (SEQ ID No30) using the pM vector harbouring the MXAN_3757mxO1ec synthetic gene providing by the supplier. The PCR product is digested and cloned between the SacI and KpnI sites of the pCL1920. The resulting plasmid is verified by DNA sequencing and called pCL1920-Ptrc01/RBS01*2-MXAN_3757mxO1ec.

Ptrc01/RBS01*2-MXAN_3757mxO1ec-SacI F (SEQ ID No29)
with

Ccgagctc<u>gagctgttgacaattaatcatccggctcgtataatg</u>

<u>tgtggaa</u>GTCGACGTTAACACGCGTtaaggaggttataaATGCC

TGAGTTTAAAGTTG sequence (lower case) for SacI restriction site and extrabases,
sequence (underlined lower case) for the trc promoter sequence (Amman et al., 1983),
sequence (upper case) for SalI, HpaI and MluI restriction sites,
sequence (bold lower case) corresponding to RBS consensus sequence with a PsiI restriction site,
sequence (italic upper case) homologous to the beginning of MXAN_3757mxO1ec synthetic gene sequence,
MXAN_3757mxO1ec-KpnI R(SEQ ID No30)
with C<u>GGGGTACC</u>TTAACGACCTTTATACACCG sequence (underlined upper case) for KpnI restriction site and extrabases,
sequence (upper case) homologous to the end of the MXAN_3757mxO1ec synthetic gene sequence.

4.3.2—Construction of pCL1920-Ptrc01/RBS01*2-MXANmxO1ec(3757-4264) Plasmid pCL1920-Ptrc01/RBS01*2-MXANmxO1ec(3757-4264) plasmid is derived from pCL1920-Ptrc01/RBS01*2-MXAN_3757mxO1ec described above and MXAN_4264mxO1ec synthetic gene described below.

MXAN_4264mxO1ec Synthetic Gene

A synthetic gene of the *Myxococcus xanthus* MXAN_4264 gene coding for a 3-methylglutaconyl-CoA decarboxylase subunit A is synthesized by Invitrogen. The codon usage and GC content of the gene is adapted to *Escherichia coli* according to the supplier's matrix. The construct is cloned into supplier's pM vectors and verified by sequencing.

MXAN_4264 gene sequence from *Myxococcus xanthus* (NC_008095) optimized for *Escherichia coli*: MXAN_4264mxO1ec contains the following sequence (SEQ ID No38):

ATGAAAACCGCACGTTGGTGTAGCCTGGAAGAAGCAGTTGCAAGCAT

TCCGGATGGTGCAAGCCTGGCAACCGGTGGTTTTATGCTGGGTCGTG

CACCGATGGCACTGGTTATGGAACTGATTGCACAGGGTAAACGTGAT

CTGGGTCTGATTAGCCTGCCGAATCCGCTGCCAGCAGAATTTCTGGT

TGCCGGTGGTTGTCTGGCACGTCTGGAAATTGCATTTGGTGCACTGA

GCCTGCAAGGTCGTGTTCGTCCGATGCCGTGTCTGAAACGTGCAATG

GAACAGGGCACCCTGGCATGGCGTGAACATGATGGTTATCGTGTTGT

TCAGCGTCTGCGTGCAGCAAGCATGGGTCTGCCGTTTATTCCGGCAC

CGGATGCAGATGTTAGTGGCCTGGCACGTACCGAACCGCCTCCGACC

GTTGAAGATCCGTTTACAGGTCTGCGTGTTGCAGTTGAACCGGCATT

-continued
```
TTATCCGGATGTTGCCCTGCTGCATGCACGTGCCGCAGATGAACGTG

GTAATCTGTATATGGAAGATCCGACCACCGATCTGCTGGTTGCGGGT

GCAGCAAAACGTGTTATTGCAACCGTGGAAGAACGTGTTGCAAAACT

GCCTCGTGCAACCCTGCCTGGTTTTCAGGTTGATCGTATTGTTCTGG

CACCGGGTGGTGCCCTGCCGACCGGTTGTGCAGGTCTGTATCCGCAT

GATGATGAAATGCTGGCACGTTATCTGAGCCTGGCAGAAACCGGTCG

TGAAGCCGAGTTTCTGGAAACCCTGCTGACCCGTCGTGCAGCATAA
```

The MXAN_4264mxO1ec synthetic gene is amplified by PCR with primers RBS01*2-MXAN_4264mxO1ec-SmaI F (SEQ ID No31) and MXAN_4264mxO1ec-BamHI R(SEQ ID No32) using the pM vector harbouring the MXAN_4264mxO1ec synthetic gene providing by the supplier. The PCR product is digested and cloned between the SmaI and BamHI sites of the pCL1920-Ptrc01/RBS01*2-MXAN_3757mxO1ec. The resulting plasmid is verified by DNA sequencing and called pCL1920-Ptrc01/RBS01*2-MXANmxO1ec(3757-4264).

RBS01*2-MXAN_4264mxO1ec-SmaI F (SEQ ID No31) with cgggggggtaccccgggTAAGGAGGTTATAAATGAAAACCGCACGTTGGTG sequence (lower case) for KpnI and SmaI restriction sites and extrabases, sequence (bold upper case) for RBS consensus sequence with a PsiI restriction site, sequence (upper case) homologous to the beginning of MXAN_4264mxO1ec synthetic gene sequence, MXAN_4264mxO1ec-BamHI R(SEQ ID No32) with <u>GCTCTAGAGGATCCT</u>TATGCTGCACGACGGGTCAG sequence (underlined upper case) for BamHI and XbaI restriction sites and extrabases, sequence (upper case) homologous to the end of the MXAN_4264mxO1ec synthetic gene sequence.

4.3.3—Construction of pCL1920-Ptrc01/RBS01*2-MXANmxO1ec(3757-4264-4265) Plasmid pCL1920-Ptrc01/RBS01*2-MXANmxO1ec(3757-4264-4265) plasmid is derived from pCL1920-Ptrc01/RBS01*2-MXANmxO1ec(3757-4264) described above and MXAN_4265mxO1ec synthetic gene described below and a transcriptional terminator.

Synthetic Gene MXAN_4265mxO1ec

A synthetic gene of the *Myxococcus xanthus* MXAN_4265 gene coding for a 3-methylglutaconyl-CoA decarboxylase subunit B is synthesized by Invitrogen. The codon usage and GC content of the gene is adapted to *Escherichia coli* according to the supplier's matrix. The construct is cloned into supplier's pM vectors and verified by sequencing.

MXAN_4265 gene sequence from *Myxococcus xanthus* (NC_008095) optimized for *Escherichia coli*: MXAN_4265mxO1ec contains the following sequence (SEQ ID No39):

```
ATGAGCGCAACCCTGGATATCACACCGGCAGAAACCGTTGTTAGCCT

GCTGGCACGTCAGATTGATGATGGTGGTGTTGTTGCAACCGGTGTTG

CAAGTCCGCTGGCAATTCTGGCCATTGCAGTTGCACGTGCCACCCAT

GCACCGGATCTGACCTATCTGGCATGTGTTGGTAGCCTGGACCCGGA

AATTCCGACCCTGCTGCCGAGCAGCGAAGATCTGGGTTATCTGGATG

GTCGTAGCGCAGAAATTACCATTCCGGACCTGTTTGATCATGCACGT

CGTGGTCGTGTTGATACCGTTTTTTTTGGTGCAGCCGAAGTTGATGC

CGAAGGTCGTACCAATATGACCGCAAGCGGTAGTCTGGATAAACCGC

GTACCAAATTTCCTGGTGTTGCCGGTGCAGCAACCCTGCGTCAGTGG

GTTCGTCGTCCGGTTCTGCTGGTTCCGCGTCAGAGCCGTCGTAATCT

GGTTCCGGAAGTTCAGGTTGCCACCACCCGTGATCCGCGTCGTCCTG

TTACCCTGATTAGCGATCTGGGTGTTTTTGAACTGGGTGCAAGCGGT

GCACGTCTGCTGGCTCGCCATCCGTGGGCAAGCGAAGAACATATTGC

AGAACGTACCGGTTTTGCATTTCAGGTTAGCGAAGCACTGAGCGTTA

CCAGCCTGCCGGATGCACGTACCGTTGCAGCAATTCGTGCAATTGAT

CCGCATGGTTATCGTGATGCACTGGTTGGTGCATAA
```

The MXAN_4265mxO1ec synthetic gene is amplified by PCR with primers RBS01*2-MXAN_4265mxO1ec-XbaI F (SEQ ID No33) and MXAN_4265mxO1ec-PstI R (SEQ ID No34) using the pM vector harbouring the MXAN_4265mxO1ec synthetic gene providing by the supplier. The PCR product is digested and cloned between the XbaI and PstI sites of the pCL1920-Ptrc01/RBS01*2-MXANmxO1ec(3757-4264). The resulting plasmid is verified by DNA sequencing and called pCL1920-Ptrc01/RBS01*2-MXANmxO1ec(3757-4264-4265).

RBS01*2-MXAN_4265mxO1ec-XbaI F (SEQ ID No33) with gctctagaTAAGGAGGTTATAAATGAGCGCAACCCTGGATATC sequence (lower case) for XbaI restriction site and extrabases, sequence (bold upper case) for RBS consensus sequence with a PsiI restriction site, sequence (upper case) homologous to the beginning of MXAN$_{13}$ 4265mxO1ec synthetic gene sequence, MXAN_4265mxO1ec-PstI R (SEQ ID No34) with <u>GCCAAGCTTCTGCAG</u>GCAGAAAGGCCCACCCGAAGGTGAGCCAGgtat
acTTATGCACCAACCAGTGCATC sequence (underlined upper case) for HindIII and PstI restriction sites and extrabases, sequence (bold upper case) for T7Te transcriptional terminator sequence from T7 phage (Harrington et al., 2011), sequence (lower case) for BstZ17I restriction site, sequence (upper case) homologous to the end of the MXAN_4265mxO1ec synthetic gene sequence.

4.4—Construction of Strain 4: MG1655 Ptrc30-atoB ΔpdhR lpd*(A55V) (pUC19-Ptrc01/OP01/RBS01-adhE2ca-RBS01*2-mvaSefO1ec-TT02) (pCL1920-Ptrc01/RBS01*2-MXANmxO1ec(3757-4264-4265)-TT07)

Construction of a strain with increased prenol pathway flux expressing the atoB gene to produce acetoacetyl-CoA, the optimized mvaS gene from *Enterococcus faecalis* to produce 3-hydroxy-3-methylglutaryl-CoA, the optimized MXAN (3757-4264-4265) operon from *Myxococcus xanthus* to produce 3-methylcrotonyl-CoA and the adhE2ca gene from *Clostridium acetobutylicum* to produce prenol.

The pUC19-Ptrc01/OP01/RBS01-adhE2ca-RBS01*2-mvaSefO1ec-TT02 and pCL1920-Ptrc01/RBS01*2-MXANmxO1ec(3757-4264-4265)-TT07 plasmids are introduced by electroporation into the strain 3 (Table 1). The presence of the two plasmids is verified and the resulting strain MG1655 Ptrc30-atoB ΔpdhR lpd*(A55V) (pUC19-Ptrc01/OP01/RBS01-adhE2ca-RBS01*2-mvaSefO1ec-TT02) (pCL1920-Ptrc01/RBS01*2-MXANmxO1ec(3757-4264-4265)-TT07) is called strain 4 (Table 1).

Example 5

Culture of the Above Described Prenol Production Strains on Glucose

Production strains 1, 2, 3 and 4 are evaluated in small Erlenmeyer flasks using modified M9 medium (Anderson, 1946, Proc. Natl. Acad. Sci. USA 32:120-128) that is supplemented with 10 $g \cdot L^{-1}$ MOPS and 10 $g \cdot L^{-1}$ glucose and adjusted to pH 6.8.

A 5 mL preculture is grown at 37° C. for 6.5 hours in a mixed medium (10% LB medium (Sigma 25%) with 2.5 $g \cdot L^{-1}$ glucose and 90% minimal medium described above). It is used to inoculate a 50 mL culture to an $OD_{600}$ of 0.1 in minimal medium. When necessary, antibiotics are added at concentrations of 50 $mg \cdot L^{-1}$ for ampicillin and spectinomycin and 10 $mg \cdot L^{-1}$ for gentamycin. The temperature of the cultures is 37° C. When the culture reaches an $OD_{600}$ of 7 to 9, extracellular metabolites are analyzed using HPLC with refractometric detection (organic acids and glucose). Production of prenol is determined by GC/MS.

The strains 2 and 4 produce prenol with a concentration ranging between 0.001 and 100 mM whereas strains 1 and 3 do not produce it.

PATENT REFERENCES

WO 2009/006429
WO 2009/076676
WO 2010/031076
US 2010/0216958
WO 2010/031076
WO 2008/052973
WO 2008/052595
WO 2008/040387
WO 2007/144346
WO 2007/141316
WO 2007/077041
WO 2007/017710
WO 2006/082254
WO 2006/082252
WO 2005/111202
WO 2005/073364
WO 2005/047498
WO 2004/076659

NON-PATENT REFERENCES

Amann E, Brosius J, Ptashne M (1983), *Gene*. 25:167-178
Amann E, Ochs B, Abel K J (1988), *Gene*. 69:301-315
Anderson E H (1946), *Proc Natl Acad Sci USA*. 32:120-128
Bode H B, Ring M W, Schwär G, Altmeyer M O, Kegler C, Jose I R, Singer M, Müller R (2009), *Chembiochem*. 10:128-140
Daschner K, Cottée I, Binder S (2001), *Plant Physiol*. 126: 601-612
Datsenko K A, Wanner B L (2000), *Proc Natl Acad Sci USA*. 97:6640-6645
Dhar A, Dhar K, Rosazza J P (2002), *J Ind Microbiol Biotechnol*. 28:81-87
Förster-Fromme K, Jendrossek D (2008), *FEMS Microbiol Lett*. 286:78-84
Gogerty D S, Bobik T A (2010), *Appl Environ Microbiol*. 76:8004-8010
Harrington K J, Laughlin R B, Liang S (2001), *Proc Natl Acad Sci USA*. 98:5019-5024
Kovach M E, Elzer P H, Hill D S, Robertson G T, Farris M A, Roop R M 2nd, Peterson K M (1995), *Gene*. 166:175-176
Lerner C G, Inouye M (1990), *Nucleic Acids Res*. 18:4631
Liebl W, Klamer R, Schleifer K H (1989), *Appl Microbiol Biotechnol*. 32:205-210
Lutz R, Bujard H (1997), *Nucleic Acids Res*. 25:1203-1210
Miller J H (1992), A Short Course in Bacterial Genetics: A Laboratory Manual and Handbook for *Escherichia coli* and Related Bacteria, Cold Spring Harbor Laboratory Press, Cold Spring Harbor, N.Y.
Mohsen A W, Navarette B, Vockley J (2001), *Mol Genet Metab*. 73:126-137
Nagai K, Thøgersen H C (1984), *Nature*. 309:810-812
Norrander J, Kempe T, Messing J (1983), *Gene*. 26:101-106
Orosz A, Boros I, Venetianer P (1991), *Eur J. Biochem*. 201: 653-659
Park J H, Kim T Y, Lee K H, Lee S Y (2011), *Biotechnol Bioeng*. 108:934-946
Perham R N, Lowe P N (1988), *Methods Enzymol*. 166:330-342
Prescott L et al. (1999), "Microbiology" 4th Edition, WCB McGraw-Hill
Riedel C, Rittmann D, Dangel P, Mockel B, Petersen S, Sahm H, Eikmanns B J (2001), *J Mol Microbiol Biotechnol*. 3:573-583
Sambrook J et al. (1989) (2001), "Molecular Cloning: A Laboratory Manual" 2nd & 3rd Editions, Cold Spring Harbor Laboratory Press
Schaefer U, Boos W, Takors R, Weuster-Botz D (1999), *Anal Biochem*. 270:88-96
Sinclair D A, Dawes I W, Dickinson J R (1993), *Biochem Mol Biol Int*. 31:911-922
Skinner D D, Morgenstern M R, Fedechko R W, Denoya C D (1995), *J. Bacteriol*. 177:183-190
Sykes P J, Burns G, Menard J, Hatter K, Sokatch J R (1987), *J. Bacteriol*. 169:1619-1625
Ward D E, Ross R P, van der Weijden C C, Snoep J L, Claiborne A (1999), *J. Bacteriol*. 181:5433-5442
Zhang Y X, Denoya C D, Skinner D D, Fedechko R W, McArthur H A, Morgenstern M R, Davies R A, Lobo S, Reynolds K A, Hutchinson C R (1999), *Microbiology*. 145: 2323-2334

The invention claimed is:

1. Method for fermentative production of prenol, comprising culturing a recombinant microorganism from Enterobacteriaceae family in a culture medium comprising a source of carbon, wherein in said microorganism, the prenol biosynthesis pathway comprises 3-methylcrotonyl-CoA as intermediate product, that is converted into prenol by action of an enzyme with alcohol dehydrogenase and aldehyde dehydrogenase activity.

2. Method according to claim 1, wherein the enzyme is an alcohol-aldehyde dehydrogenase (AdhE).

3. Method according to claim 2, wherein the AdhE enzyme is heterologous.

4. Method according to claim 3, wherein the AdhE enzyme has a specificity for the substrate 3-methylcrotonyl-CoA.

5. Method according to claim 2, wherein the AdhE enzyme is AdhE2 from *Clostridium acetobutylicum*.

6. Method according to claim 1, wherein the biosynthesis pathway of 3-methyl-crotonyl-CoA from pyruvate and acetyl-CoA includes the following intermediate products: 4-methyl-2-oxopentanoate and 3-methylbutanoyl-CoA.

7. Method according to claim 6, wherein at least one of the following enzymes is overexpressed: an acetolactate synthase, a keto-acid reductoisomerase, a dihydroxy-acid dehydratase, a 2-isopropylmalate synthase, a 2-isopropylmalate hydrolyase, a 3-isopropylmalate dehydrogenase, a branched chain keto acid dehydrogenase complex and an acyl-CoA dehydrogenase.

8. Method according to claim 7, wherein two enzymes are overexpressed: an heterologous branched chain keto acid dehydrogenase complex and an heterologous acyl-CoA dehydrogenase.

9. Method according to claim 1, wherein the biosynthesis pathway of 3-methyl-crotonyl-CoA from pyruvate and acetyl-CoA includes the following intermediate products: 3-hydroxy-3-methylglutaryl-CoA and 3-methylglutaconyl-CoA.

10. Method according to claim 9, wherein at least one of the following enzymes is overexpressed: an acetyl-CoA C-acetyltransferase, a HMG-CoA synthase, a 3-methylglutaconyl-CoA hydratase, a 3-methylglutaconyl-CoA decarboxylase.

11. Method for the fermentative production of prenol according to claim 1, wherein the microorganism is from the species *Escherichia coli* or *Corynebacterium glutamicum*.

12. Method for the fermentative production of prenol according to claim 1, comprising isolation of the prenol from the culture medium.

13. Method for production of isoprene, comprising:
culturing a recombinant microorganism from Enterobacteriaceae family in a culture medium comprising a source of carbon, wherein in said microorganism, the prenol biosynthesis pathway comprises 3-methylcrotonyl-CoA as intermediate product that is converted into prenol by action of an enzyme with alcohol dehydrogenase activity and aldehyde dehydrogenase activity, and performing chemical dehydration of bio-produced prenol into isoprene.

14. A genetically modified microorganism for fermentative production of prenol according to claim 1 wherein said microorganism overexpresses at least one enzyme selected from the group consisting of:

an acetolactate synthase, a keto-acid reductoisomerase, a dihydroxy-acid dehydratase, a 2-isopropylmalate synthase, a 2-isopropylmalate hydrolyase, a 3-isopropylmalate dehydrogenase, a branched chain keto acid dehydrogenase complex and an acyl-CoA dehydrogenase, an acetyl-CoA C-acetyltransferase, a HMG-CoA synthase, a 3-methylglutaconyl-CoA hydratase, and a 3-methylglutaconyl-CoA decarboxylase.

* * * * *

SEQUENCE LISTING

<160> NUMBER OF SEQ ID NOS: 39

<210> SEQ ID NO 1
<211> LENGTH: 130
<212> TYPE: DNA
<213> ORGANISM: Artificial Sequence
<220> FEATURE:
<223> OTHER INFORMATION: Oligonucleotide

<400> SEQUENCE: 1

```
taggatccat caaaatttag gaggttagtt agaatgtggt cacatcctca atttgaaaaa    60
ggtagtggtg gtggtagtgg tggtggtagt cccgggatcg aagggcgcat gaaagttaca   120
aatcaaaaag                                                          130
```

<210> SEQ ID NO 2
<211> LENGTH: 36
<212> TYPE: DNA
<213> ORGANISM: Artificial Sequence
<220> FEATURE:
<223> OTHER INFORMATION: Oligonucleotide

<400> SEQUENCE: 2

```
taagtggcgc cttaaaatga ttttatatag atatcc                              36
```

<210> SEQ ID NO 3
<211> LENGTH: 30
<212> TYPE: DNA
<213> ORGANISM: Artificial Sequence
<220> FEATURE:
<223> OTHER INFORMATION: Oligonucleotide

<400> SEQUENCE: 3

```
tactggctag catacaaaaa atgggacggc                                     30
```

<210> SEQ ID NO 4
<211> LENGTH: 32
<212> TYPE: DNA
<213> ORGANISM: Artificial Sequence
<220> FEATURE:
<223> OTHER INFORMATION: Oligonucleotide

<400> SEQUENCE: 4

```
agcaaggatc cgcagaaagg cccacccgaa gg                                  32
```

<210> SEQ ID NO 5
<211> LENGTH: 109
<212> TYPE: DNA
<213> ORGANISM: Artificial Sequence
<220> FEATURE:
<223> OTHER INFORMATION: Oligonucleotide

<400> SEQUENCE: 5

```
ttctgcggat ccgagctgtt gacaattaat catccggctc gtataatgtg tggaagtcga    60
cgttaaccct aggtaaggag gttataaatg gatcatcgtc tgacaccgg               109
```

<210> SEQ ID NO 6
<211> LENGTH: 98
<212> TYPE: DNA
<213> ORGANISM: Artificial Sequence
<220> FEATURE:
<223> OTHER INFORMATION: Oligonucleotide

<400> SEQUENCE: 6

```
ggtcgactct agaaacagat aaaacgaaag gcccagtctt tcgactgagc ctttcgtttt    60
```
atttgatgag atctttaacc caccagaccc agttcgcg                                    98

<210> SEQ ID NO 7
<211> LENGTH: 90
<212> TYPE: DNA
<213> ORGANISM: Artificial Sequence
<220> FEATURE:
<223> OTHER INFORMATION: Oligonucleotide

<400> SEQUENCE: 7
gccgctctag aactagtgag ctgttgacaa ttaatcatcc ggctcgtata atgtgtggaa           60
gtcgacgtta accaaatacc cgagcgagcg                                            90

<210> SEQ ID NO 8
<211> LENGTH: 67
<212> TYPE: DNA
<213> ORGANISM: Artificial Sequence
<220> FEATURE:
<223> OTHER INFORMATION: Oligonucleotide

<400> SEQUENCE: 8
taccgggccc ctcgaggcag aaaggcccac ccgaaggtga gccagtcaga tatgcagggc           60
gtggccc                                                                    67

<210> SEQ ID NO 9
<211> LENGTH: 83
<212> TYPE: DNA
<213> ORGANISM: Artificial Sequence
<220> FEATURE:
<223> OTHER INFORMATION: Oligonucleotide

<400> SEQUENCE: 9
taacaattta cgtagctcag ccggcactag tgaattcatt aaagaggaga aaggtaccat           60
gagccagcaa gtcattattt tcg                                                  83

<210> SEQ ID NO 10
<211> LENGTH: 123
<212> TYPE: DNA
<213> ORGANISM: Artificial Sequence
<220> FEATURE:
<223> OTHER INFORMATION: Oligonucleotide

<400> SEQUENCE: 10
tccttatacg tattccacac agtatacgag ccggatgatt aatcgtcaac agctcgggcc           60
cgcagaaagg cccacccgaa ggtgagccag gtcgacttaa ttcataaacg caggttgttt          120
tgc                                                                       123

<210> SEQ ID NO 11
<211> LENGTH: 48
<212> TYPE: DNA
<213> ORGANISM: Artificial Sequence
<220> FEATURE:
<223> OTHER INFORMATION: Oligonucleotide

<400> SEQUENCE: 11
ggccacggta aagatgcgct tgatcaggtg gatatcgtcg ctaactac                        48

<210> SEQ ID NO 12
<211> LENGTH: 48
<212> TYPE: DNA
<213> ORGANISM: Artificial Sequence
<220> FEATURE:

<223> OTHER INFORMATION: Oligonucleotide

<400> SEQUENCE: 12
gtagttagcg acgatatcca cctgatcaag cgcatcttta ccgtggcc        48

<210> SEQ ID NO 13
<211> LENGTH: 39
<212> TYPE: DNA
<213> ORGANISM: Artificial Sequence
<220> FEATURE:
<223> OTHER INFORMATION: Oligonucleotide

<400> SEQUENCE: 13
tcgggcccgg atcccattta cgttgacacc atcgaatgg        39

<210> SEQ ID NO 14
<211> LENGTH: 95
<212> TYPE: DNA
<213> ORGANISM: Artificial Sequence
<220> FEATURE:
<223> OTHER INFORMATION: Oligonucleotide

<400> SEQUENCE: 14
acttaaggag ctcaacagat aaaacgaaag gcccagtctt tcgactgagc ctttcgtttt        60
atttgatgta cgtcactgcc cgcttttcca g tcggg        95

<210> SEQ ID NO 15
<211> LENGTH: 137
<212> TYPE: DNA
<213> ORGANISM: Artificial Sequence
<220> FEATURE:
<223> OTHER INFORMATION: Oligonucleotide

<400> SEQUENCE: 15
gcatcactgc cctgctcttc tccggtgtca ttttcgtcat tggtttaacg ctgttctgac        60
ggcaccccta caaacagaag gaatataaac tggctcacct tcgggtgggc ctttctgctg        120
taggctggag ctgcttc        137

<210> SEQ ID NO 16
<211> LENGTH: 128
<212> TYPE: DNA
<213> ORGANISM: Artificial Sequence
<220> FEATURE:
<223> OTHER INFORMATION: Oligonucleotide

<400> SEQUENCE: 16
ccgatagcag tacgtaccgc actgacgatg acacaatttt tcatttataa cctccttatt        60
ccacacagta tacgagccgg atgattaatc gtcaacagct ccatggtcca tatgaatatc        120
ctccttag        128

<210> SEQ ID NO 17
<211> LENGTH: 18
<212> TYPE: DNA
<213> ORGANISM: Artificial Sequence
<220> FEATURE:
<223> OTHER INFORMATION: Oligonucleotide

<400> SEQUENCE: 17
ccatcaatac cgtcaacc        18

<210> SEQ ID NO 18
<211> LENGTH: 19

```
<212> TYPE: DNA
<213> ORGANISM: Artificial Sequence
<220> FEATURE:
<223> OTHER INFORMATION: Oligonucleotide

<400> SEQUENCE: 18
cataaacctg tccgtctcc                                              19

<210> SEQ ID NO 19
<211> LENGTH: 127
<212> TYPE: DNA
<213> ORGANISM: Artificial Sequence
<220> FEATURE:
<223> OTHER INFORMATION: Oligonucleotide

<400> SEQUENCE: 19
catcttctgg ataattttta ccagaaaaat cactaattct ttcgttgctc cagtgtaggc    60
tggagctgct tcgaagttcc tatactttct agagaatagg aacttcagag cgcttttgaa   120
gctgggg                                                            127

<210> SEQ ID NO 20
<211> LENGTH: 128
<212> TYPE: DNA
<213> ORGANISM: Artificial Sequence
<220> FEATURE:
<223> OTHER INFORMATION: Oligonucleotide

<400> SEQUENCE: 20
gaccaattga cttcggcaag tggcttaaga caggaactca tgattccggg gatccgtcga    60
cctgcagttc gaagttccta ttctctagaa agtataggaa cttcttcaag atcccctcac   120
gctgccgc                                                           128

<210> SEQ ID NO 21
<211> LENGTH: 21
<212> TYPE: DNA
<213> ORGANISM: Artificial Sequence
<220> FEATURE:
<223> OTHER INFORMATION: Oligonucleotide

<400> SEQUENCE: 21
gaatgtattt acccacggca g                                            21

<210> SEQ ID NO 22
<211> LENGTH: 20
<212> TYPE: DNA
<213> ORGANISM: Artificial Sequence
<220> FEATURE:
<223> OTHER INFORMATION: Oligonucleotide

<400> SEQUENCE: 22
gcacgctcaa caccttcttc                                              20

<210> SEQ ID NO 23
<211> LENGTH: 112
<212> TYPE: DNA
<213> ORGANISM: Artificial Sequence
<220> FEATURE:
<223> OTHER INFORMATION: Oligonucleotide

<400> SEQUENCE: 23
cccgaaagcg aagaagaagt aattttttcgt tgccggaac atccggcaat taaaaaagcg    60
gctaaccacg ccgcttttttt tacgtctgca agtgtaggct ggagctgctt cg          112
```

```
<210> SEQ ID NO 24
<211> LENGTH: 106
<212> TYPE: DNA
<213> ORGANISM: Artificial Sequence
<220> FEATURE:
<223> OTHER INFORMATION: Oligonucleotide

<400> SEQUENCE: 24
ccatactgtc aggctgaata acgagcaacg gtcagcagta tgcgaacgtc tctctgaacg     60
tggagcaaga agactggaaa ggtaaacata tgaatatcct ccttag                  106

<210> SEQ ID NO 25
<211> LENGTH: 20
<212> TYPE: DNA
<213> ORGANISM: Artificial Sequence
<220> FEATURE:
<223> OTHER INFORMATION: Oligonucleotide

<400> SEQUENCE: 25
ggtggtggtt agggtattac                                                20

<210> SEQ ID NO 26
<211> LENGTH: 19
<212> TYPE: DNA
<213> ORGANISM: Artificial Sequence
<220> FEATURE:
<223> OTHER INFORMATION: Oligonucleotide

<400> SEQUENCE: 26
cgtggagcaa gaagactgg                                                 19

<210> SEQ ID NO 27
<211> LENGTH: 40
<212> TYPE: DNA
<213> ORGANISM: Artificial Sequence
<220> FEATURE:
<223> OTHER INFORMATION: Oligonucleotide

<400> SEQUENCE: 27
gctctagata aggaggttat aaatgaccat tggcatcgac                          40

<210> SEQ ID NO 28
<211> LENGTH: 30
<212> TYPE: DNA
<213> ORGANISM: Artificial Sequence
<220> FEATURE:
<223> OTHER INFORMATION: Oligonucleotide

<400> SEQUENCE: 28
ctagctagct tagttacgat agctacgcac                                     30

<210> SEQ ID NO 29
<211> LENGTH: 102
<212> TYPE: DNA
<213> ORGANISM: Artificial Sequence
<220> FEATURE:
<223> OTHER INFORMATION: Oligonucleotide

<400> SEQUENCE: 29
ccgagctcga gctgttgaca attaatcatc cggctcgtat aatgtgtgga agtcgacgtt     60
aacacgcgtt aaggaggtta taaatgcctg agtttaaagt tg                      102

<210> SEQ ID NO 30
<211> LENGTH: 29
```

```
<212> TYPE: DNA
<213> ORGANISM: Artificial Sequence
<220> FEATURE:
<223> OTHER INFORMATION: Oligonucleotide

<400> SEQUENCE: 30
cggggtacct taacgacctt tatacaccg                                       29

<210> SEQ ID NO 31
<211> LENGTH: 51
<212> TYPE: DNA
<213> ORGANISM: Artificial Sequence
<220> FEATURE:
<223> OTHER INFORMATION: Oligonucleotide

<400> SEQUENCE: 31 cgggggtac ccccgggtaa ggaggttata atgaaaacc gcacgttggt g                51

<210> SEQ ID NO 32
<211> LENGTH: 35
<212> TYPE: DNA
<213> ORGANISM: Artificial Sequence
<220> FEATURE:
<223> OTHER INFORMATION: Oligonucleotide

<400> SEQUENCE: 32
gctctagagg atccttatgc tgcacgacgg gtcag                                35

<210> SEQ ID NO 33
<211> LENGTH: 43
<212> TYPE: DNA
<213> ORGANISM: Artificial Sequence
<220> FEATURE:
<223> OTHER INFORMATION: Oligonucleotide

<400> SEQUENCE: 33
gctctagata aggaggttat aaatgagcgc aaccctggat atc                       43

<210> SEQ ID NO 34
<211> LENGTH: 71
<212> TYPE: DNA
<213> ORGANISM: Artificial Sequence
<220> FEATURE:
<223> OTHER INFORMATION: Oligonucleotide

<400> SEQUENCE: 34
gccaagcttc tgcaggcaga aaggcccacc cgaaggtgag ccaggtatac ttatgcacca     60
accagtgcat c                                                          71

<210> SEQ ID NO 35
<211> LENGTH: 1161
<212> TYPE: DNA
<213> ORGANISM: Artificial Sequence
<220> FEATURE:
<223> OTHER INFORMATION: acdH gene from Streptomyces avermitilid
      optimized for E. coli

<400> SEQUENCE: 35
atggatcatc gtctgacacc ggaactggaa gaactgcgtc gtaccgttga agaatttgca     60
catgatgttg ttgcaccgaa atcggcgat tctatgaac gtcatgaatt cccgtatgaa      120
attgtgcgtg aaatgggtcg tatgggtctg tttggtctgc cgtttccgga agaatatggt    180
ggtatgggtg tgattatct ggcactgggt attgccctgg aagaactggc acgtgttgat     240
agcagcgttg caattaccct ggaagccggt gttagcctgg gtgcaatgcc gattcacctg    300
```

```
tttggcaccg atgcacagaa agcagaatgg ctgcctcgtc tgtgtagcgg tgaaattctg    360
ggtgcatttg gtctgaccga accggatggt ggtagtgatg ccggtgcaac ccgtaccacc    420
gcacgtctgg atgaaagcac caatgaatgg gttattaatg caccaaatg cttcattacc     480 aatagcggca ccgatatcac cggtctggtt accgttaccg cagttaccgg tcgtaaacct    540
gatggtaaac cgctgattag cagcattatt gttccgagcg gtacaccggg ttttaccgtt    600
gcagcaccgt atagcaaagt tggttggaat gcaagcgata cccgtgaact gagctttgca    660
gatgttcgtg ttccggcagc aaatctgctg ggtgaacagg tcgtggtta tgcacagttt     720 ctgcgtatcc tggatgaagg tcgtattgca attagcgcac tggcaacagg tctggcacag    780
ggttgtgttg atgaaagcgt taaatatgca ggcgaacgcc atgcctttgg tcgtaatatt    840
ggtgcatatc aggcaatcca gtttaaaatc gcagatatgg aaatgaaagc ccatatggca    900
cgcgttggtt ggcgtgatgc agcaagccgt ctggttgccg gtgaaccgtt caaaaaagaa    960
gcagcaattg caaaactgta tagcagtacc gttgccgttg ataatgcacg tgaagcaacc   1020
cagattcatg gtggttatgg ttttatgaat gaatatccgg ttgcacgtat gtggcgtgat   1080
agcaaaattc tggaaattgg tgaaggcacc agcgaagttc agcgtatgct gattgcacgc   1140
gaactgggtc tggtgggtta a                                              1161
```

<210> SEQ ID NO 36
<211> LENGTH: 1152
<212> TYPE: DNA
<213> ORGANISM: Artificial Sequence
<220> FEATURE:
<223> OTHER INFORMATION: mvaS gene from Enterococcus faecalis optimized
      for E. coli

<400> SEQUENCE: 36

```
atgaccattg gcatcgacaa aatcagcttt tttgttccgc cttactatat cgacatgacc     60
gcactggccg aagcacgtaa tgttgatccg ggtaaatttc atattggtat tggtcaggat    120
cagatggccg ttaatccgat tagccaggat attgttacct tgcagcaaa tgcagcagaa     180 gcaattctga ccaaagaaga taagaagcc atcgatatgg ttattgttgg caccgaaagc    240
agcattgatg aaagcaaagc agccgcagtt gttctgcatc gtctgatggg tattcagccg    300
tttgcacgta gctttgaaat taagaagca tgttacggcg caaccgcagg tctgcagctg    360
gcaaaaaatc atgttgcact gcatccggat aaaaaagttc tggttgttgc agcagatatc    420
gccaaatatg gtctgaatag cggtggtgaa ccgacccagg gtgccggtgc agttgcaatg    480
ctggttgcaa gcgaaccgcg tattctggca ctgaaagagg ataatgttat gctgacgcag    540
gatatctatg attttggcg tccgaccggt catccgtatc cgatggttga tggtccgctg    600
agcaatgaaa cctatattca gagctttgca caggtgtggg atgaacataa aaaacgtacc    660
ggtctggatt cgcagatta tgatgcactg gcctttcata ttccgtacac caaaatgggt    720
aaaaaagcac tgctggccaa aattagcgat cagaccgaag ccgaacaaga acgtatcctg    780
gcacgttatg aagaaagcat tatctatagc cgtcgtgtgg gtaatctgta caccggtagc    840
ctgtatctgg gtctgattag cctgctgaa atgcaaccca ccctgaccgc tggtaatcag    900
attggtctgt ttagctatgg tagcggtgcc gttgcagaat ttttcacagg tgaactggtt    960
gcaggttatc agaatcatct gcagaaagaa acccatctgg ccctgctgga taatcgtacc   1020
gaactgagca ttgcagaata tgaagcaatg tttcagaaaa ccctggatac cgatattgat   1080
cagaccctgg aagatgaact gaaatatagc attagcgcca ttaataacac cgtgcgtagc   1140
```
tatcgtaact aa                                                     1152

<210> SEQ ID NO 37
<211> LENGTH: 777
<212> TYPE: DNA
<213> ORGANISM: Artificial Sequence
<220> FEATURE:
<223> OTHER INFORMATION: MXAN 3757 gene from Myxococcus xanthus
      optimized for E. coli

<400> SEQUENCE: 37

| | | | | | | |
|---|---|---|---|---|---|---|
| atgcctgagt | ttaaagttga | tgcacgtggt | ccgattgaaa | tttggaccat | tgatggtgaa | 60 |
| agccgtcgta | atgcaattag | ccgtgcaatg | ctgaaagaac | tgggtgaact | ggttacccgt | 120 |
| gttagcagca | gccgtgatgt | tcgtgcagtt | gttattaccg | gtgccggtga | taaagcattt | 180 |
| tgtgccggtg | ccgatctgaa | agaacgtgca | acaatggccg | aagatgaagt | tcgtgcattt | 240 |
| ctggatggtc | tgcgtcgtac | ctttcgtgca | attgaaaaaa | gcgattgcgt | ttttattgcc | 300 |
| gcaattaatg | gtgcagcact | gggtggtggc | accgaactgg | cactggcatg | tgatctgcgt | 360 |
| gttgcagcac | cggcagcgga | actgggtctg | accgaagtta | aactgggcat | tattccgggt | 420 |
| ggtggtggta | cacagcgtct | ggcacgtctg | gttggtccgg | tcgtgcaaa | agatctgatt | 480 |
| ctgaccgcac | gtcgtattaa | tgcagcagaa | gcatttagcg | ttggtctggc | aaatcgcctg | 540 |
| gcaccggaag | tcatctgct | ggcagttgcc | tatggtctgg | ccgaaagcgt | tgttgaaaat | 600 |
| gcaccgattg | cagttgcaac | cgccaaacat | gcaattgatg | aaggcaccgg | tctggaactg | 660 |
| gatgatgcac | tggccctgga | actgcgtaaa | tatgaagaaa | ttctgaaaac | cgaagatcgc | 720 |
| ctggaaggcc | tgcgtgcatt | tgcagaaaaa | cgtgcaccgg | tgtataaagg | tcgttaa | 777 |

<210> SEQ ID NO 38
<211> LENGTH: 798
<212> TYPE: DNA
<213> ORGANISM: Artificial Sequence
<220> FEATURE:
<223> OTHER INFORMATION: MXAN 4264 gene from Myxococcus xanthus
      optimized for E. coli
<220> FEATURE:
<221> NAME/KEY: variation
<222> LOCATION: (1)..(798)
<223> OTHER INFORMATION: Optimized for E. coli

<400> SEQUENCE: 38

| | | | | | | |
|---|---|---|---|---|---|---|
| atgaaaaccg | cacgttggtg | tagcctggaa | gaagcagttg | caagcattcc | ggatggtgca | 60 |
| agcctggcaa | ccgtggtttt | tatgctgggt | cgtgcaccga | tggcactggt | tatggaactg | 120 |
| attgcacagg | gtaaacgtga | tctgggtctg | attagcctgc | cgaatccgct | gccagcagaa | 180 |
| tttctggttg | ccggtggttg | tctggcacgt | ctggaaattg | catttggtgc | actgagcctg | 240 |
| caaggtcgtg | ttcgtccgat | gccgtgtctg | aaacgtgcaa | tggaacaggg | caccctggca | 300 |
| tggcgtgaac | atgatggtta | tcgtgttgtt | cagcgtctgc | gtgcagcaag | catgggtctg | 360 |
| ccgtttattc | cggcaccgga | tgcagatgtt | agtggcctgg | cacgtaccga | accgcctccg | 420 |
| accgttgaag | atccgtttac | aggtctgcgt | gttgcagttg | aaccggcatt | ttatccggat | 480 |
| gttgccctgc | tgcatgcacg | tgccgcagat | gaacgtggta | atctgtatat | ggaagatccg | 540 |
| accaccgatc | tgctggttgc | gggtgcagca | aaacgtgtta | ttgcaaccgt | ggaagaacgt | 600 |
| gttgcaaaac | tgcctcgtgc | aaccctgcct | ggttttcagg | ttgatcgtat | tgttctggca | 660 |
| ccgggtggtg | ccctgccgac | cggttgtgca | ggtctgtatc | cgcatgatga | tgaaatgctg | 720 |

```
                                    -continued gcacgttatc tgagcctggc agaaaccggt cgtgaagccg agtttctgga aaccctgctg      780
acccgtcgtg cagcataa                                                   798

<210> SEQ ID NO 39
<211> LENGTH: 741
<212> TYPE: DNA
<213> ORGANISM: Artificial Sequence
<220> FEATURE:
<223> OTHER INFORMATION: MXAN 4265 gene from Myxococcus xanthus
      optimized for E. coli

<400> SEQUENCE: 39
atgagcgcaa ccctggatat cacaccggca gaaaccgttg ttagcctgct ggcacgtcag       60
attgatgatg gtggtgttgt tgcaaccggt gttgcaagtc cgctggcaat tctggccatt      120
gcagttgcac gtgccaccca tgcaccggat ctgacctatc tggcatgtgt tggtagcctg      180
gacccggaaa ttccgaccct gctgccgagc agcgaagatc tgggttatct ggatggtcgt      240
agcgcagaaa ttaccattcc ggacctgttt gatcatgcac gtcgtggtcg tgttgatacc      300
gttttttttg gtgcagccga agttgatgcc gaaggtcgta ccaatatgac cgcaagcggt      360
agtctggata aaccgcgtac caaatttcct ggtgttgccg gtgcagcaac cctgcgtcag      420
tgggttcgtc gtccggttct gctggttccg cgtcagagcc gtcgtaatct ggttccggaa      480
gttcaggttg ccaccaccgg tgatccgcgt cgtcctgtta ccctgattag cgatctgggt      540
gtttttgaac tgggtgcaag cggtgcacgt ctgctggctc gccatccgtg ggcaagcgaa      600
gaacatattg cagaacgtac cggttttgca tttcaggtta gcgaagcact gagcgttacc      660
agcctgccgg atgcacgtac cgttgcagca attcgtgcaa ttgatccgca tggttatcgt      720
gatgcactgg ttggtgcata a                                                741
```